US009993620B2

(12) United States Patent
Le et al.

(10) Patent No.: US 9,993,620 B2
(45) Date of Patent: Jun. 12, 2018

(54) CATHETER ANCHORING DEVICE AND METHOD

(71) Applicant: SafeSharp Technologies Corporation, Shrewsbury, MA (US)

(72) Inventors: Duc Hong Le, Shrewsbury, MA (US); Minhhia Ngan Le, Shrewsbury, MA (US); James A. Grasfield, Sharon, MA (US); Bill Russell Alexander, Shrewsbury, MA (US)

(73) Assignee: SafeSharp Technologies Corporation, Shrewsbury, MA (US)

( * ) Notice: Subject to any disclaimer, the term of this patent is extended or adjusted under 35 U.S.C. 154(b) by 622 days.

(21) Appl. No.: 14/318,487

(22) Filed: Jun. 27, 2014

(65) Prior Publication Data

US 2015/0005733 A1 Jan. 1, 2015

Related U.S. Application Data

(60) Provisional application No. 61/841,048, filed on Jun. 28, 2013.

(51) Int. Cl.
*A61M 25/02* (2006.01)
(52) U.S. Cl.
CPC ....... *A61M 25/02* (2013.01); *A61M 2025/028* (2013.01); *A61M 2025/0286* (2013.01)
(58) Field of Classification Search
CPC ............ A61M 25/02; A61M 2025/028; A61M 2025/0286; A61M 39/1011; A61M 2025/024
See application file for complete search history.

(56) References Cited

U.S. PATENT DOCUMENTS 3,068,869 A * 12/1962 Sheiden ................. A61B 17/08
606/216
3,068,889 A * 12/1962 Swenson ................. A23G 9/20
137/386

(Continued)

FOREIGN PATENT DOCUMENTS

ES           2336354 T3    4/2010
WO      WO 93/16751 A1    9/1993

OTHER PUBLICATIONS

International Search Report and Written Opinion dated Dec. 23, 2014 from corresponding International Application No. PCT/US2014/044742.

(Continued)

*Primary Examiner* — Bhisma Mehta
*Assistant Examiner* — Jenna Zhang
(74) *Attorney, Agent, or Firm* — Wolf, Greenfield & Sacks, P.C.

(57) ABSTRACT

Methods and apparatus for anchoring a catheter to a patient's skin using a catheter anchoring device are described. The catheter anchoring device includes one or more pairs of sharps with a sharpened end configured to pierce the surface of the skin. A locking mechanism for the sharps is used as a failsafe mechanism. The catheter anchoring device further includes a catheter clamp for securing a catheter to the catheter anchoring device. Releasing the clamp allows an operator to reposition and secure the catheter at the new position without moving the catheter anchoring device.

28 Claims, 21 Drawing Sheets

(56) References Cited

U.S. PATENT DOCUMENTS

| | | | |
|---|---|---|---|
| 4,164,943 A * | 8/1979 | Hill | A61M 25/02 128/DIG. 26 |
| 4,317,451 A * | 3/1982 | Cerwin | A61B 17/0644 227/19 |
| 4,821,939 A | 4/1989 | Green | |
| 4,930,674 A | 6/1990 | Barak | |
| 5,304,183 A | 4/1994 | Gourlay et al. | |
| 5,425,489 A * | 6/1995 | Shichman | A61B 17/0643 227/108 |
| 5,490,856 A | 2/1996 | Person et al. | |
| 5,520,664 A * | 5/1996 | Bricault, Jr. | A61F 2/30767 604/174 |
| 5,540,648 A * | 7/1996 | Yoon | A61B 17/3403 600/102 |
| 5,618,311 A | 4/1997 | Gryskiewicz | |
| 5,620,452 A | 4/1997 | Yoon | |
| 5,833,695 A | 11/1998 | Yoon | |
| 6,248,117 B1 | 6/2001 | Blatter | |
| 6,544,271 B1 | 4/2003 | Adams et al. | |
| 6,572,587 B2 * | 6/2003 | Lerman | A61M 25/02 604/174 |
| 7,794,471 B1 | 9/2010 | Bender et al. | |
| 2001/0056216 A1 | 12/2001 | Lerman et al. | |
| 2001/0056261 A1 | 12/2001 | Lerman et al. | |
| 2003/0014064 A1 | 1/2003 | Blatter | |
| 2003/0045890 A1 | 3/2003 | Crainich | |
| 2003/0078596 A1 | 4/2003 | Banbury et al. | |
| 2004/0215217 A1 | 10/2004 | Banbury et al. | |
| 2004/0249391 A1 | 12/2004 | Cummins | |
| 2005/0049618 A1 | 3/2005 | Masuda et al. | |
| 2005/0075657 A1 | 4/2005 | Bombard et al. | |
| 2005/0107807 A1 | 5/2005 | Nakao | |
| 2005/0149064 A1 | 7/2005 | Peterson et al. | |
| 2005/0274768 A1 | 12/2005 | Cummins et al. | |
| 2005/0283119 A1 * | 12/2005 | Uth | A61M 39/0208 604/175 |
| 2006/0122635 A1 | 6/2006 | Naegeli et al. | |
| 2006/0135988 A1 | 6/2006 | Peterson | |
| 2006/0151568 A1 | 7/2006 | Weller et al. | |
| 2007/0213585 A1 | 9/2007 | Monassevitch et al. | |
| 2009/0054843 A1 * | 2/2009 | Lundqvist | A61M 5/1415 604/177 |
| 2009/0054916 A1 | 2/2009 | Meier et al. | |
| 2009/0206127 A1 | 8/2009 | Danielson et al. | |
| 2010/0042140 A1 | 2/2010 | Cunningham | |
| 2010/0217314 A1 * | 8/2010 | Holsten | A61B 17/0643 606/220 |
| 2012/0116427 A1 | 5/2012 | Raza | |
| 2012/0209217 A1 * | 8/2012 | Gray | G05D 7/0647 604/244 |
| 2014/0148789 A1 | 5/2014 | Le et al. | |
| 2014/0309687 A1 * | 10/2014 | Atkinson | A61B 17/08 606/218 |

OTHER PUBLICATIONS

International Search Report and Written Opinion for Application No. PCT/US2012/037032 dated Aug. 16, 2012.
International Preliminary Report on Patentability for Application No. PCT/US2014/037032 dated Nov. 21, 2013.
International Preliminary Report on Patentability for Application No. PCT/US2014/044742 dated Jan. 7, 2016.
Extended European Search Report for Application No. EP 14818572.1 dated Jan. 11, 2017.

* cited by examiner

CATHETER ANCHORING DEVICE AND METHOD

RELATED APPLICATIONS

This application claims priority under 35 U.S.C. § 119(e) to U.S. Provisional Application Ser. No. 61/841,048, entitled "CATHETER ANCHORING DEVICE AND METHOD" filed on Jun. 28, 2013, which is herein incorporated by reference in its entirety.

BACKGROUND

Technical Field

The present disclosure relates to medical devices and more particularly to the process of anchoring medical catheters to the skin of human patients to prevent movement of a catheter after insertion into the body. The catheter anchors described may also be used in a similar fashion for veterinary use.

Discussion of the Related Art

One of the most common medical procedures performed each year is the insertion of catheters into the body for the purpose of delivering fluids to or extracting fluids from a specific part of the body and/or extracting air from a specific part of the body. Examples of catheters include but are not limited to central venous catheters (CVC) which deliver fluids intravenously to a vein typically in the chest, neck, or groin; peripherally inserted central catheters (PICC lines) which deliver fluids intravenously typically in the arms; chest tubes which extract fluids and/or air from the chest cavity; gastrostomy tubes (G-tubes) which deliver fluids to the stomach; jejunostomy tubes (J-tubes) which deliver fluids to the jejunum; and Hickman catheters which are used in chemotherapy and hemodialysis. An additional type of catheter uses a wire to deliver current to a specific part of the body. A trans-venous pacemaker wire that is placed temporarily into the heart is an example of a wire-based catheter that delivers current to the heart instead of fluids. Each of these and other catheters and lines that enter into the body should be stably anchored to the patient's skin so that their precise placement into the vein, heart, chest cavity, stomach, jejunum, etc. is not disturbed by movement of the patient so that the catheter or line can achieve its intended delivery or extraction purpose. Furthermore, it is important that the catheter or line remain in its inserted location to prevent damage to the patient including tearing of the skin, dislodging of the catheter, rupturing of the vein, accidental removal, or other consequential damage from the unintended movement of the catheter. For this purpose, typically a catheter anchor is attached to the patient's skin near the catheter or line insertion site, and the catheter or line is mechanically tethered to this anchor to prevent the catheter or line from being moved or disturbed.

A common methodology for anchoring the catheter or line to the patient's skin is the use of a catheter anchor that can be sutured to the patient's skin. These catheter anchors come in various sizes and configurations to accommodate catheters of different diameters and some are affixed directly to the catheters themselves, but they typically work in the same fashion. They are typically applied by a physician due to the skill needed to suture them to the patient. In typical use a physician will insert a catheter into a patient to a particular depth or position. Next the physician will place a form-fitting non-slip pliable sleeve typically made of silicone around the catheter near the insertion point into the body. The physician then places, for example, a hard plastic cap that is keyed to the silicone sleeve over the sleeve. This cap typically has two holes that are parallel to the patient's skin when in position. Once the cap is in position, the physician will suture the cap using a straight or curved exposed needle and non-dissolvable suture thread to the patient's skin using the two holes in the cap. The physician should be careful not to penetrate the skin too deeply so as not cause excessive bleeding, nerve damage, or other physical damage to the patient but should also penetrate deeply enough to securely anchor the catheter. The suturing process involves inserting the needle through the skin on each side of the cap, drawing the suture threads through the skin, and then tying the loops of thread to each side of the catheter via their respective holes. Due to the dangers associated with the open needle, it is critical that the patient remain still during the insertion procedure. The process of attaching the catheter to the patient's skin in ideal circumstances takes approximately 3 minutes after the catheter has been properly positioned. If a patient is not still during the procedure, then the suturing process can take considerably longer. After the physician completes the suturing process, medical adhesive tape is then applied over the sutured catheter anchor to further secure the catheter anchor and to cover the puncture wounds made by the needle to reduce the risk of contamination and subsequent infection. Once the catheter anchor has been sutured to the patient, it is difficult to move or adjust the catheter. The exact position of the catheter is almost always verified by x-ray. If the physician needs to reposition the catheter at all (which happens frequently), then the physician has to cut and remove the sutures, remove the catheter anchor cap, reposition the catheter, and repeat the entire suturing process as described above. This results in additional wounds in the patient's skin and tissue, consequently multiplying the risk of infection or the aforementioned other risks to the patient. A catheter anchor as described can usually remain in place on a patient's skin for a limited time (typically up to a week). During that time, the wound area created by the needle punctures and the catheter insertion site must be cleaned as frequently as necessary with a disinfecting cleaning solution such as Betadine to reduce the risk of infection to the patient. Millions of catheters of all different sizes and types are inserted into patients in the US every year, most requiring at least one catheter anchor per insertion.

There are several safety risks to both the physician and the patient involved with the insertion of a typical sutured catheter anchor. One risk is a needlestick injury to the physician. If the physician who is wearing protective surgical gloves comes in contact with the patient's blood via puncturing of the physician's skin by the infected needle, the physician may contract any number of diseases born by the patient. In some cases this may lead to a chronic or life-threatening disease including HIV infection or Hepatitis which are passed from one human to another by blood to blood contact. The risks associated with a needlestick injury can be very serious. In many hospitals, it is a requirement that a physician undergo expensive testing for possible infection whenever there is a contaminated or suspected contaminated needlestick injury. The risk of a needlestick injury is significant when using an unprotected needle even when the patient is completely still. If a patient is agitated or unstable, the risk of a needlestick injury is greatly increased due to the unpredictable motion of the patient. A patient can also be subject to a needlestick injury if the physician unwittingly punctures his or her skin during the suturing process and then contaminates the patient with the infected needle.

Needlestick injuries have become a very serious health risk for medical professionals. According to the CDC, more than 800,000 needlestick injuries take place in the US alone each year, and this number does not reflect the numerous needlestick injuries that go unreported. Of these 800,000 needlestick injuries, more than 380,000 happen to hospital-based medical personnel, resulting in more than 1,000 cases of serious infections to physicians or other medical practitioners every year.

Therefore, any measure that can reduce needlestick injuries is both potentially lifesaving and highly cost effective. Due to the serious risks associated with needlestick injuries including blood-borne infections of fatal and incurable diseases, Congress enacted the US Needlestick Safety and Prevention Act which mandates the use of safer alternative methodologies to conventional needles whenever it is possible to do so. Insurance companies also follow the same safety guidelines.

Another significant risk to the patient during and after the insertion of a sutured catheter anchor is infection. While the physician takes great care not to contaminate the needle or the wound sites made by the needle, infections can and do enter the patient's bloodstream via the wound sites. This can lead to significant complications for the patient depending on the type of infection and the patient's health, and in some cases may become life-threatening or lead to death. Reducing infection is important during the insertion of any catheter and catheter anchor. Any time a needle enters, exits, and then re-enters the skin, the risk of contamination increases, and consequently the risk of infection to the patient increases. Additionally, each time a needle enters the skin, a new wound site is generated; and with each additional wound site, the risk of infection increases. Therefore, the drawing of the exposed needle or suture thread through the patient's skin and out again increases the risk of infection to the patient by both increasing the number of wound sites and by potentially drawing contaminants into the patient's skin which can come in contact with the patient's bloodstream. This can even occur when the suturing process is conducted in a clean hospital environment.

The risk of damage done by the insertion of the needle is yet another safety issue. Even a skilled physician can damage the patient's skin, underlying tissue, nerves, blood vessels, or worse if the patient moves unexpectedly during the time that the needle has penetrated the patient's body. The needle insertion typically is only done between a depth of 3 and 5 mm below the surface of the skin (depending on the insertion location on the body) to reduce bleeding and nerve pain or damage which takes great care and skill by the physician. Given the typical time that is needed to suture a catheter anchor and the numerous types of conditions under which a catheter anchor might be applied, it is not uncommon for the needle to cause an injury to the patient which could be minor or significant. Older patients who have very thin skin (i.e. shallow epidermis and dermis layers) and minimal fat tissue in the subcutaneous layer of the skin (hypodermis) are particularly at risk for this type of injury especially for catheter insertions in the neck.

The depth of penetration into the skin is an important factor for patient comfort and for mitigating consequential damage such as excessive bleeding and tearing of the skin. The top two layers of the skin (the epidermis and dermis layers) are typically 2-4 mm in depth depending on the location on the body. Since the majority of the nerve endings lie at the junction of the epidermis and dermis layers, it is desirable to penetrate through the dermis layer and into the subcutaneous layer of the skin to avoid excessive discomfort and to reduce the risk of tearing the skin while the catheter anchor is in place. Penetrating the skin deep into the subcutaneous layer runs the risk of reaching the underlying muscle layer or bone depending on the insertion location, and excessive bleeding may occur due to the presence of larger blood vessels, veins, and arteries. The depth of the skin will also vary based on the age of the patient (due to decreased amounts of fat cells), the general health of the patient, and the body mass index of the patient. The skin in the neck, for example, is most frequently thinner than the skin in the chest. Therefore, it would be desirable to have a reliable penetration depth of the sharps to reduce the aforementioned negative consequences of a needle insertion, while maximizing the holding strength of the catheter anchor.

There have been numerous attempts to create alternative catheter anchors to the common sutured catheter anchor. One type uses an adhesive backed base which adheres to the patient's skin. While no needles or sharps are employed in this methodology, the drawbacks to this type of catheter anchor are significant. First, the adhesive can cause significant irritation to the skin of some patients. Second, removal of the adhered catheter anchor can cause significant damage to the patient's skin including tearing, and the removal process can be slow and painstaking, sometimes requiring the use of harsh chemicals. Third, adhesive-type catheter anchors are difficult to apply to wet, sweaty, or compromised skin. And the nature of the adhesive makes it not strong enough to hold most sizes of catheters on the patient's skin, making it suitable only for normally taped applications such as PICC lines. Some manufacturers of these adhesive-type catheter anchors acknowledge their weaknesses in their own instruction literature and recommend them only for use as a substitute for taped applications, making them unsuitable for catheter applications that normally require sutured catheter anchors.

Another type of catheter anchor employs a single-sided sharp or set of sharps that penetrate the skin and then re-emerge through the skin to lock into a plastic base which contains the anchoring mechanism for the catheter. U.S. Pat. No. 6,572,587 to Lerman et al. teaches one such method. U.S. Pat. No. 7,914,498 to Daniels, Jr. et al teaches another very similar method. In these examples and others, the exposed tip of the sharp which exits the skin to engage with the housing during insertion into the patient's skin becomes a potential risk for infection to the patient. While the tip of the sharp is exposed to the air (i.e. during the entire time the catheter anchor is attached to the patient) it may be exposed to contaminants. In order to remove the catheter anchor from the patient, the exposed portion of the sharp is drawn back underneath the skin and through the underlying tissue, potentially exposing the contaminated tip to the patient's bloodstream and increasing the risk of infection over the common suturing methodology.

One significant reason that sharp or needle-based catheter anchors have not been successful in supplanting the sutured catheter anchor is that none have solved the issue of eliminating or significantly reducing needlestick injuries. These types of catheter anchors can cause needlestick injuries either before, during, or after insertion, and this lack of full protection against needlestick injuries may be responsible for the lack of adoption of these methodologies. Lerman et al. describes the shortcomings of numerous prior art catheter anchors that fail to protect the operators and patients from needlestick injuries. Lerman et al. also claims to have reduced the risk of needlestick injury with its invention, but Lerman lacks any failsafe mechanism to prevent a needlestick injury during insertion or removal. Furthermore, once the contaminated device has been removed from a patient, there is nothing to prevent the operator or any other person who may come in contact with the device from deploying its sharps and potentially incurring a needlestick injury. In addition, there is no mechanism that prevents the reuse of the device which could cause grave injury after contamination. In fact, Lerman et al. even teaches that its device may be re-inserted into a patient's skin after removal as a methodology for anchoring if a catheter has to be repositioned. Daniels, Jr. et al. does not even mention the risks of needlestick injuries nor teaches any methodology to reduce the risk of needlestick injuries.

SUMMARY

In nearly all medical procedures improvements in speed are beneficial to improving the efficiency of the delivery of care for medical practitioners—especially physicians. Moreover, improvements in speed of a medical procedure can be life-saving in trauma and triage situations in the hospital, in the field, or in battlefield situations. Embodiments of the present disclosure substantially improve the speed and reliability of the insertion of a catheter anchoring device.

Embodiments can prevent the sharps from being deployed accidentally during the insertion process. Embodiments can also lock the points of the sharps within the device securely before the device is removed from the surface of the patient's skin thereby reducing any chance of a needlestick injury to the operator and/or any subsequent personnel who come in contact with it.

An important factor for patient comfort after insertion is the relative positions of the pointed ends of the sharps. If the pointed ends of the sharps remain free after insertion under the skin, then the patient may experience discomfort during movement akin to having a splinter imbedded in the skin known as the "splinter effect." To eliminate the splinter effect, an embodiment has the point of each pair of opposing sharps nest into each other. This nesting prevents the sharp point of each needle from irritating the patient's skin while inserted. This essentially closed arc has the further benefit of creating a stronger anchor than even a surgical staple where the points nearly meet but do not overlap.

With a patient completely motionless, it typically takes a skilled physician approximately three minutes to completely attach a sutured catheter anchor to the patient once a catheter has been inserted into the body. If the patient is agitated or less than ideal conditions are present, this process can take considerably longer. The catheter anchor should also be precisely placed before suturing, as it is difficult to reposition the catheter after the catheter anchor is sutured into place. When using a sutured catheter anchor the greatest risk from the procedure, particularly one in which the patient is not motionless, is an inadvertent needlestick injury. Any attempt to speed up the process of inserting the catheter anchor using an unprotected needle (e.g. in a trauma situation where time is of the essence) greatly increases the chances of a needlestick injury.

The embodiments overcome several shortcomings of the sutured catheter. First, the insertion process of the embodiments nominally takes only about 10-15 seconds in total to fasten the catheter anchor to the patient's skin and to secure the catheter to the catheter anchor. Second, once the catheter anchor is secured, the catheter can be repositioned as often as needed by releasing the catheter clamping mechanism, repositioning the catheter to its new desired position, and then relocking the catheter clamping mechanism which also takes just a matter of seconds to accomplish. Third, the sharps are not exposed to the physician or other medical personnel at any time. The sharps can only be deployed when the catheter anchor is lying on the surface of the patient's skin and the catheter has already been inserted into the patient (due to the catheter anchor's interlock mechanism), preventing the sharps from penetrating anything but the patient's skin. During the time that the catheter anchor is attached to the patient, the sharps are nested safely in pairs below the patient's skin under the catheter anchor. During the removal process, the sharps are retracted automatically via a spring-loaded mechanism, and the tips of the sharps become permanently and completely encased within the catheter anchor housing before the catheter anchor can be lifted from the patient's skin. Therefore, there is no time when the ends of the sharps are exposed to the physician or other medical personnel, eliminating any chance of a needlestick injury.

This substantial increase in speed of insertion yields numerous benefits. In trauma and triage situations, the time savings can be critical to the patient's survival. In nearly all situations, the physician will save valuable time to perform other procedures and duties, increasing his/her efficiency. If a patient is not completely motionless, the substantial increase in speed enables the physician to insert the catheter anchor in a matter of seconds—dramatically reducing the risk of injury to the patient or physician over conventional suturing. In any instance where a catheter needs to be repositioned or adjusted after insertion (which happens frequently), the time savings is quite substantial as the sutured catheter anchor would have to be removed and a new one sutured in its place in the new position, wasting a significant amount of time. Embodiments of the present disclosure, which do not have to be removed to allow for the re-positioning of the catheter, obviate these risks.

Embodiments also provide for easy and reliable insertion into a patient. As previously described, the depth of penetration into the skin is very important to reduce the risk of injury and/or discomfort to the patient. Suturing with a conventional straight or curved needle within the confines of that very shallow and specific depth takes great skill, patience, and dexterity; and this procedure is typically only performed by physicians. Embodiments greatly simplify the insertion process and make the insertion more reliable. The depth of penetration of the curved sharps is preset to fall within the narrow range of the dermis and subcutaneous layer of the skin depending on the location of insertion on the body (i.e. approximately 4-5 mm at full depth) so that the practitioner does not have to worry about penetrating the skin too shallowly or too deeply, consequently eliminating the risks associated with penetration outside of the desired safe range. The operator need not have the skill or dexterity that a physician who sutures would have, for the difficulty and precision of an unprotected needle insertion is eliminated. This makes embodiments suitable for anchoring all types of catheters including PICC lines. In addition, embodiments can be applied quickly when time is of the essence such as in trauma situations. The reliability of operation of the embodiments extends to patients with lacerated or damaged skin, patients who are agitated, patients who have wet or sweaty skin, and patients with an abundance of hair on their skin. Thus, regardless of the location of insertion, the condition of the patient's skin, and the motion of the patient, the operator can quickly, easily, and reliably insert the catheter anchor securely and safely into the patient and secure the catheter in place. Since the position of the catheter is fully adjustable after the catheter anchor has been inserted, the precision of placement associated with a conventional sutured catheter is obviated.

Another advantage of the embodiments is that they provide a completely self-contained device which does not require any additional insertion or extraction instruments or tools. The self-contained catheter anchor reduces the chances of contamination and consequent infection since the sharps are only exposed as they are being deployed into the patient's skin. Unlike a conventional sutured catheter anchor or a stapled catheter anchor (such as taught by U.S. Pat. No. 5,730,758 to Allgeyer) there are no exposed sharps or needles and no tools which may be dropped or contaminated during the insertion or extraction process. Furthermore, any tools or additional materials (such as the needle or suture) needed to insert the catheter anchor could be lost or misplaced during the procedure, further slowing the process of insertion or extraction. Proprietary tools or instruments are also likely to increase the cost of the procedure.

The embodiments add other benefits to the process of anchoring catheters to patients. The embodiments provide a device for attaching an apparatus to a body which:

(a) Can be securely attached to the body without the risk of a needlestick injury to the physician or patient;
(b) Can be safely detached from the patient's body without the risk of a needlestick injury to the physician or patient;
(c) Is completely self-contained and does not require additional implements for insertion or removal;
(d) Reduces the risk of infection;
(e) Can be securely attached very quickly and safely on all types of skin surfaces regardless of the physical motion of the patient;
(f) Can be removed quickly and safely on all types of skin surfaces without harming the patient's skin;
(g) Can quickly and reliably secure a catheter in place;
(h) Has the ability to allow the catheter to be released for readjustment or movement and then re-secured without detaching the device from the patient's skin as many times as needed;
(i) Has a predictable and reliable insertion depth into the patient's skin which minimizes discomfort to the patient during the insertion process and during the entire duration of its attachment to the patient;
(j) Is small and compact so it will be less obtrusive to the patient, will not interfere with care of the patient, and will not inhibit the movement or mobility of the patient;
(k) Can be operated easily and reliably by an operator with straightforward training;
(l) Contains a mechanical failsafe interlock mechanism which prevents the sharps from deploying until the device is properly placed on the patient's skin and the catheter is in place;
(m) Contains a mechanical failsafe interlock mechanism that automatically secures the sharps safely within the housing permanently upon actuating the removal mechanism and that prevents any reuse or accidental injury from the device;
(n) Can be deployed by the operator with a single hand (either right or left);
(o) Can be utilized for a wide range of catheters of various diameters and types; and
(p) Can be produced reliably and inexpensively so as to make it disposable.

Embodiments work in conjunction with many prior art catheters of any size or type. A catheter is first inserted into its desired area of the body of a patient by the appropriate means. Once the catheter is in place, the operator places the apparatus over the catheter on the surface of the skin of the patient in the desired insertion location. Using a squeezing motion of the operator's thumb and forefinger, the operator depresses the buttons on either end of the device which in turn precisely deploy two sets of diametrically opposed sharps into the patient's skin at a controlled depth, securely affixing the device to the patient's body. The catheter is then locked into place on the device by deploying the catheter locking mechanism. At any time, the operator may reposition the catheter by releasing the catheter locking mechanism, repositioning the catheter, and re-engaging the catheter locking mechanism. The apparatus does not have to be removed from the patient's skin to permit repositioning or readjustment of the catheter.

The apparatus can be easily and quickly removed from a patient's skin when the operator desires to do so. After the operator releases two safety mechanisms (which prevent accidental deployment), the diametrically opposed sharps instantly, automatically, and safely retract into the housing of the device, and the pointed ends of the sharps are permanently and safely contained within the housing so that no one can come in contact with them. The removed device can be safely disposed of with or without the catheter attached.

Embodiments contain multiple failsafe mechanisms to virtually eliminate the risk of needlestick injuries before the device is attached to the patient's skin, during the insertion process, during the entire time it is attached to the patient's skin, during removal from the patient's skin, and after the device has been removed from the patient's skin. Consequently, neither the operator nor anyone else is at risk for a needlestick injury at any time through the use of the device.

Embodiments vastly improve on the speed and safety with which a catheter anchor can be attached to a patient's skin over suturing methodology. Embodiments also significantly improve the speed and safety with which a catheter may be re-secured to the patient's skin after the catheter has been repositioned over the suturing methodology. Furthermore, the embodiments are easier and more reliable to operate than a conventional sutured catheter anchor, and embodiments reduce the risk of infection over a conventional sutured catheter.

Other objects and advantages of the embodiments will become apparent from the following description of the embodiments in conjunction with the accompanying drawings. Reference numbers identifying the same parts are used throughout the drawings.

According to one embodiment described herein, an anchor device is provided. The anchor device comprises a housing having a bottom surface and at least one pair of sharps within the housing. Each sharp in the at least one pair of sharps has an end configured to pierce a skin surface. The anchor device further comprises a locking mechanism configured to maintain the end of each sharp within the housing when the locking mechanism is engaged and to enable each sharp to protrude from the bottom surface and to pierce a skin surface when the locking mechanism is disengaged.

In some embodiments, the locking mechanism is disengaged by contacting the bottom surface to the skin surface. In some embodiments, the locking mechanism is disengaged by a catheter.

In some embodiments, the anchor device further comprises at least one button configured to be pressed by an operator to move the at least one pair of sharps when the locking mechanism is disengaged. In some embodiments, the at least one button moves parallel to the bottom surface of the housing.

In some embodiments, the ends of each pair of sharps contact each other underneath the skin surface. In some embodiments, the ends of each pair of sharps are configured to be nested. In some embodiments, the ends of each pair of sharps touch at a depth from the skin surface. In some embodiments, the depth corresponds to a dermis layer. In some embodiments, the depth corresponds to a subcutaneous layer. In some embodiments, the depth corresponds to the range of approximately 4 millimeters to approximately 5 millimeters.

In some embodiments, the anchor device further comprises a cavity configured to position a catheter and a catheter locking mechanism configured to secure the catheter within the cavity when the catheter locking mechanism is engaged and to allow the catheter to be repositioned when the catheter locking mechanism is disengaged. In some embodiments, the catheter locking mechanism is engaged after the end of each sharp pierces the skin surface. In some embodiments, the catheter locking mechanism includes securing the catheter between an inner surface of the cavity and a catheter clamp. In some embodiments, the cavity is scaled to fit a dimension of the catheter.

In some embodiments, the anchor device further comprises at least one release mechanism configured to retract the end of each sharp into the housing. In some embodiments, the end of each sharp is permanently contained within the housing when the at least one release mechanism is engaged. In some embodiments, the at least one release mechanism includes a release bar having a first position and a second position, when the release bar is positioned from the first position to the second position the end of each sharp retracts into the housing. In some embodiments, the release bar permanently resides in the second position after being positioned from the first position to the second position. In some embodiments, the at least one pair of sharps retract simultaneously into the housing.

In some embodiments, the at least one pair of sharps have a radial configuration. In some embodiments, the at least one pair of sharps have a linear configuration. In some embodiments, the at least one pair of sharps have a helical configuration.

In some embodiments, the bottom surface includes a membrane and the end of each sharp is configured to pierce the membrane. In some embodiments, the membrane is silicone.

In some embodiments, the sharps are stainless steel. In some embodiments, the sharps are coated with a layer of nickel.

According to another embodiment described herein, the anchor device comprises a housing having a bottom surface, a cavity in the bottom surface, a locking pin configured to displace away from the bottom surface further into the housing in response to an object being disposed in the cavity when the bottom surface contacts a skin surface, and at least one pair of sharps within the housing. Each sharp in the at least one pair of sharps has an end configured to pierce the skin surface.

A further embodiment described herein is directed to an anchoring method. The method comprises placing an anchoring device having a bottom surface on a skin surface where the bottom surface contacts the skin surface, releasing a locking mechanism of the anchoring device, extending at least one pair of sharps from the bottom surface of the anchoring device, and piercing the skin surface with the at least one pair of sharps when the locking mechanism is released, each sharp in the at least one pair of sharps having an end configured to pierce the skin surface.

In some embodiments, the method further comprises moving the at least one pair of sharps to have each pair of sharps meet at a depth below the skin surface. In some embodiments, the locking mechanism is released by displacing a locking pin with a catheter.

In some embodiments, the method further comprises pressing at least one button on the anchoring device when the locking mechanism is released to engage the end of each sharp to pierce the skin surface.

In some embodiments, the method further comprises pressing at least one button on the anchoring device to release the locking mechanism by gathering skin in a cavity in the bottom surface of the anchoring device and displacing a locking pin by the gathered skin.

In some embodiments, the method further comprises positioning a catheter in a cavity in the anchoring device and engaging a catheter locking mechanism to secure the catheter to the catheter anchoring device. In some embodiments, the method further comprises releasing the catheter locking mechanism to unlock the catheter's position. In some embodiments, the method further comprises repositioning the catheter to a new position and re-engaging the catheter locking mechanism to secure the catheter at the new position.

In some embodiments, the method further comprises retracting the end of each sharp into the anchoring device. In some embodiments, the retracting permanently maintains the end of each sharp in the anchoring device.

DETAILED DESCRIPTION

Figure 1:
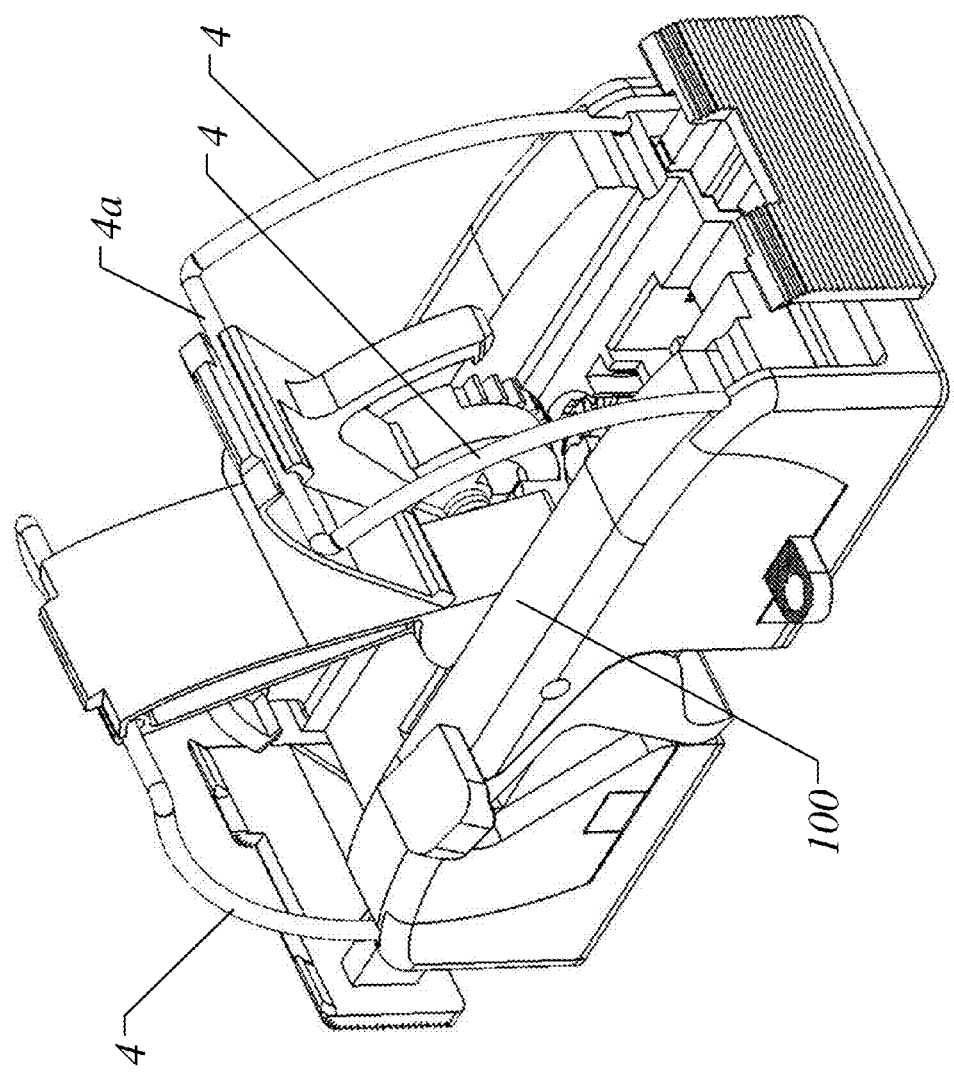
FIG. 1 is a perspective view of a catheter anchoring device in the undeployed position according to one embodiment.
Figure 3:
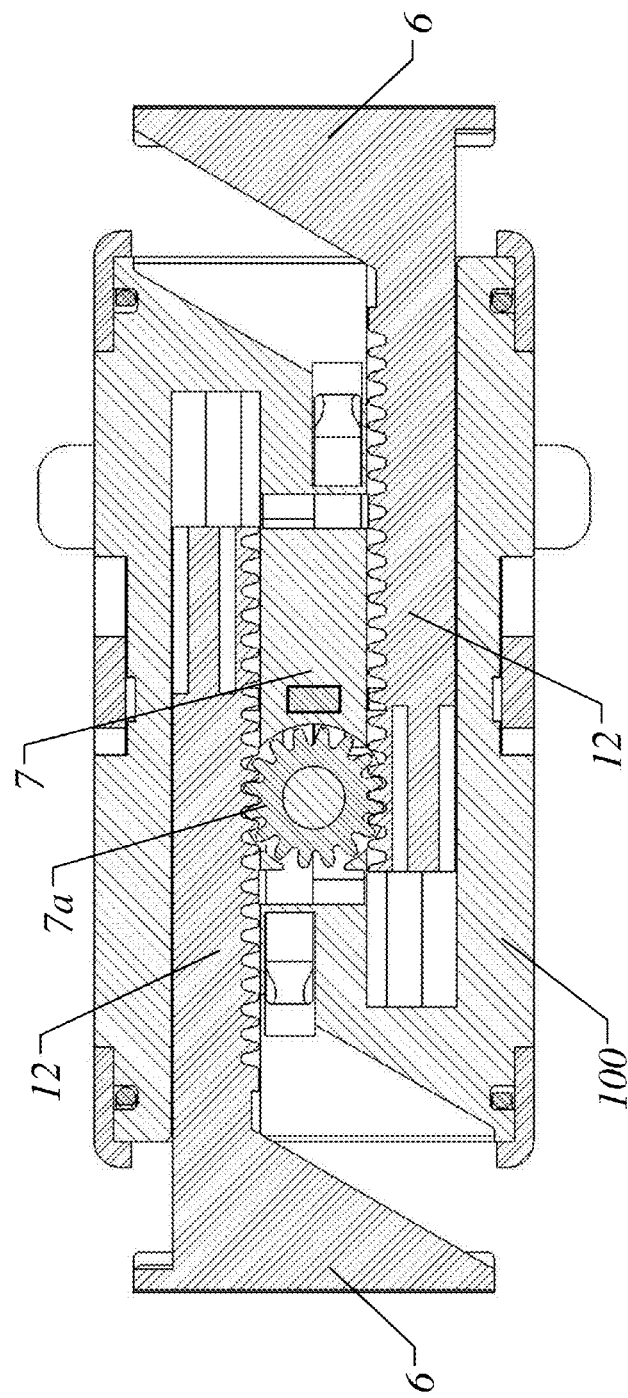
FIG. 3 is a longitudinal cross-sectional bottom view of the catheter anchoring device of FIG. 1 in the undeployed position.
Figure 4:
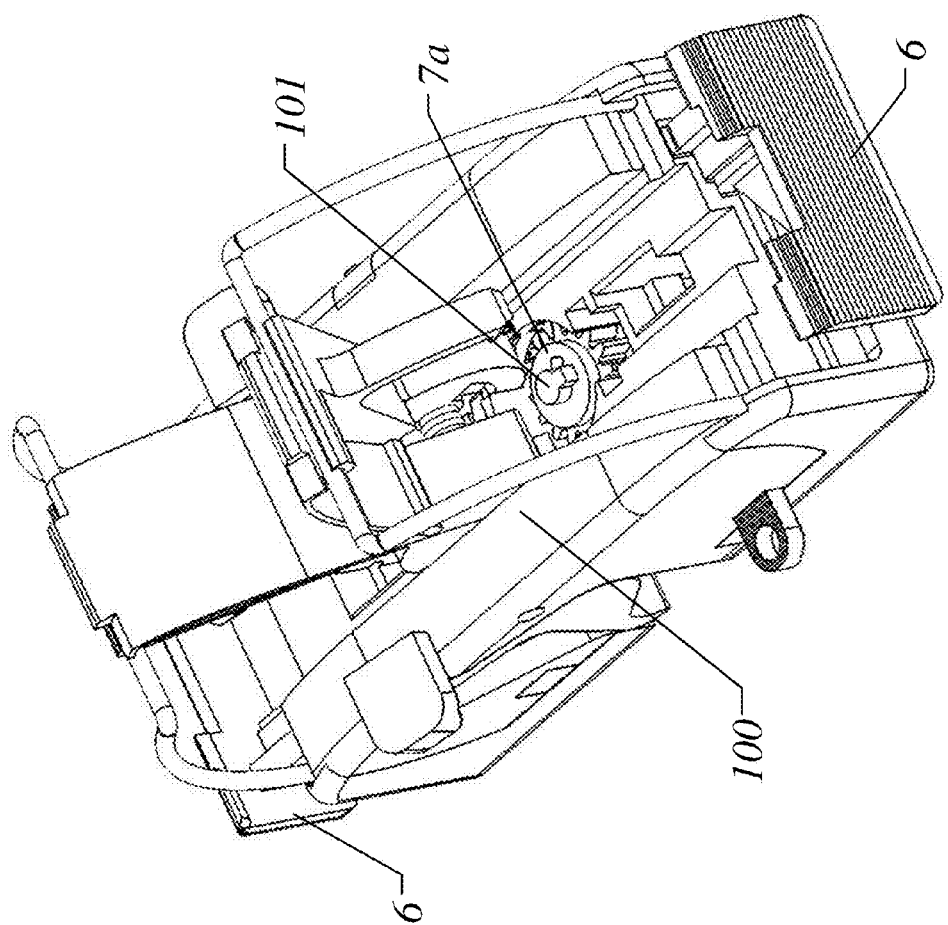
FIG. 4 is another perspective view of the catheter anchoring device of FIG. 1 in the undeployed position.
Figure 5:
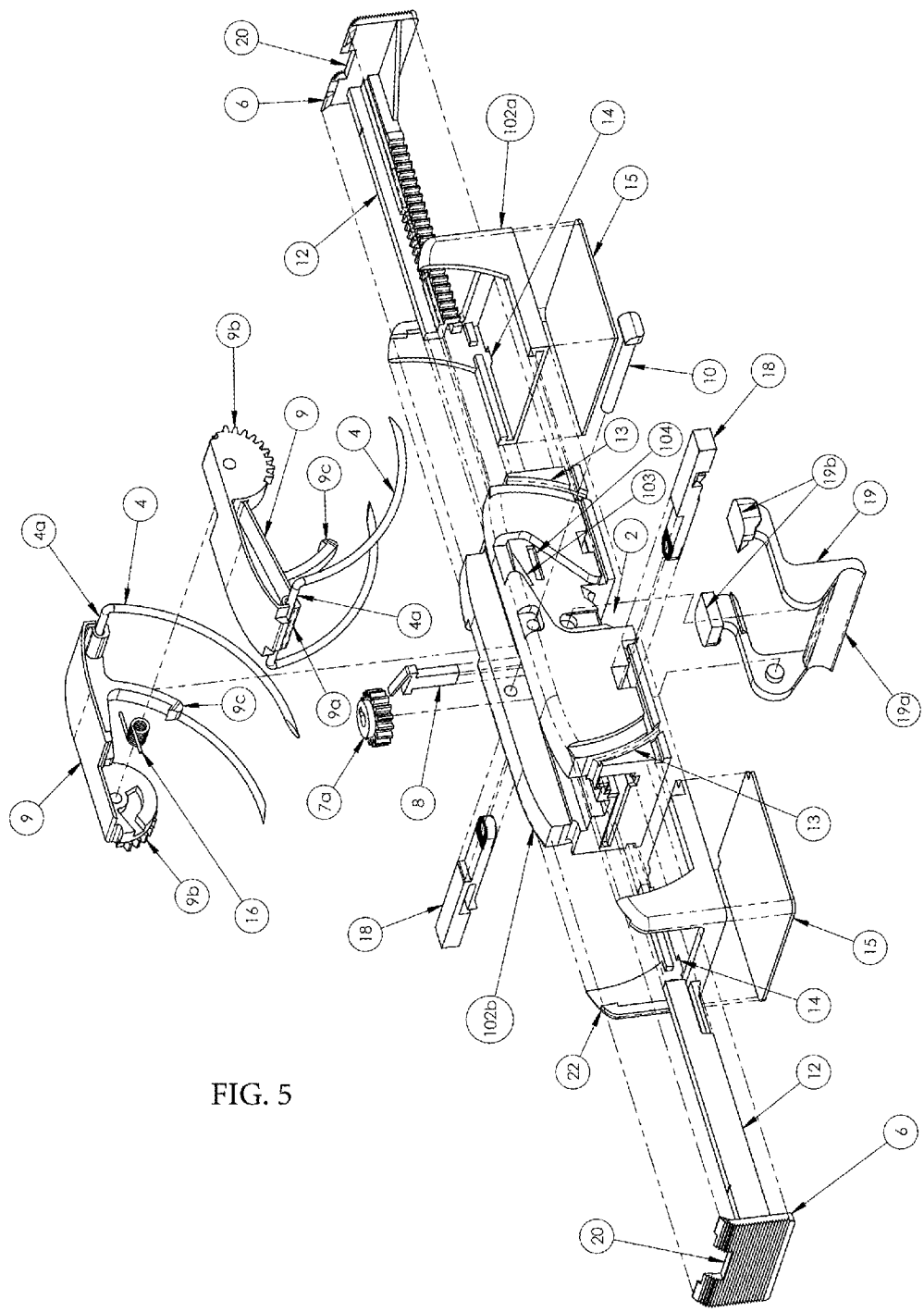
FIG. 5 is an exploded view of the catheter anchoring device of FIG. 1.

FIG. 1 is a perspective view of a catheter anchoring device in the undeployed position according to one embodiment. The pointed ends of each pair of parallel radial sharps 4 are fully enclosed within housing 100 of the catheter anchoring device as shown in the cross-sectional side view of the catheter anchoring device in FIG. 2. Each pair of two parallel radial sharps 4 are joined by a common crossbar 4a which is anchored to a pivoting wing 9 via a tang 9a integrated into pivoting wing 9. In one embodiment of the catheter anchoring device each pair of radial sharps 4 and their respective crossbar 4a are formed from a continuous piece of wire stock. Alternatively, each individual radial sharp 4 can be joined by a separate crossbar member. The pointed ends of each radial sharp 4 are sharpened in opposite directions to each other shown in FIG. 2 and are sharpened to easily penetrate a patient's skin with light pressure. Two buttons 6 are diametrically opposed to each other on opposite ends of the catheter anchoring device and linked through a pair of parallel racks 12 and a pinion gear 7a shown as item 7 in FIG. 3, and both racks 12 are linked together through the common rotation of pinion gear 7a. Pinion gear 7a is held in place by and rotates about a keyed vertical axle 101 integrated into housing 100 which enables the pinion gear 7a to be inserted into the assembled catheter anchoring device. The key in vertical axle 101 in turn prevents vertical movement of pinion gear 7a after rotation caused by the assembly of racks 12 as shown in FIG. 4. Each button 6 is an integral member of one end of rack 12 and perpendicular to the rack. Reference is made to FIG. 5 which is an exploded diagram of the catheter anchoring device. Catheter locking pin 8 contains an integral leaf spring which applies downward force toward the bottom of housing 100 in its unsprung position and prohibits the turning of pivoting wings 9 when the catheter channel 2 is empty (i.e. no catheter is present) by mechanically interfering with the rotation of pivoting wings 9. It should be noted that caps 102a and 102b, in one embodiment, are slid into place onto housing 100 and locked in place during the assembly process to become integral members of housing 100.

Figure 6:
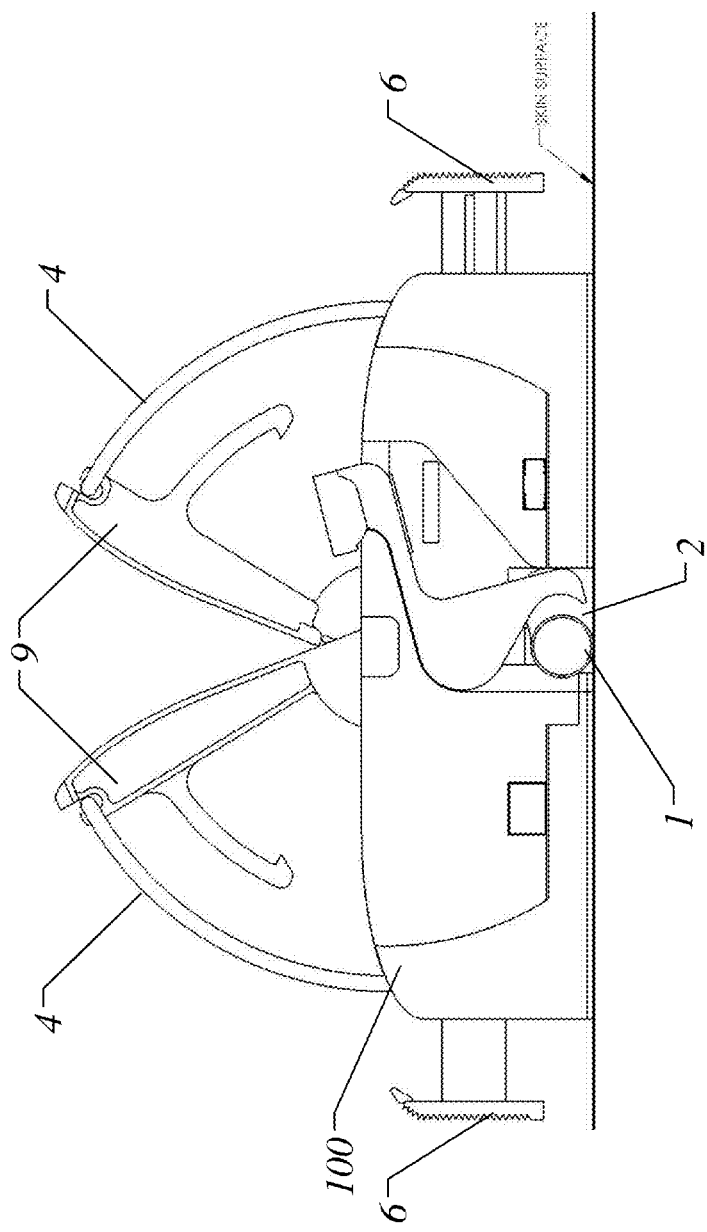
FIG. 6 is a side view of the catheter anchoring device of FIG. 1 on the surface of a patient's skin with a catheter in the catheter channel prior to deployment.

When a catheter 1 (i.e. one which conveys fluids, gases, or electrical current or any combination thereof) of correct diameter is placed in catheter channel 2 and the bottom surface of the catheter anchoring device is pressed against the surface of the skin of a patient by the operator (as shown in FIG. 6), the catheter locking pin 8 will be displaced upward orthogonal to the bottom surface of housing 100, compressing its integral leaf spring and disengaging the locking channel in both pivoting wings 9 thus allowing the rotation of pivoting wings 9. The rotation of pivoting wings 9 allows the racks 12 to move inward into housing 100 when buttons 6 are pressed inward parallel to the surface of the patient's skin. Pinion gear 7a keeps the two racks 12 and two pivoting wings 9 in synchronization with one another.

Figure 2:
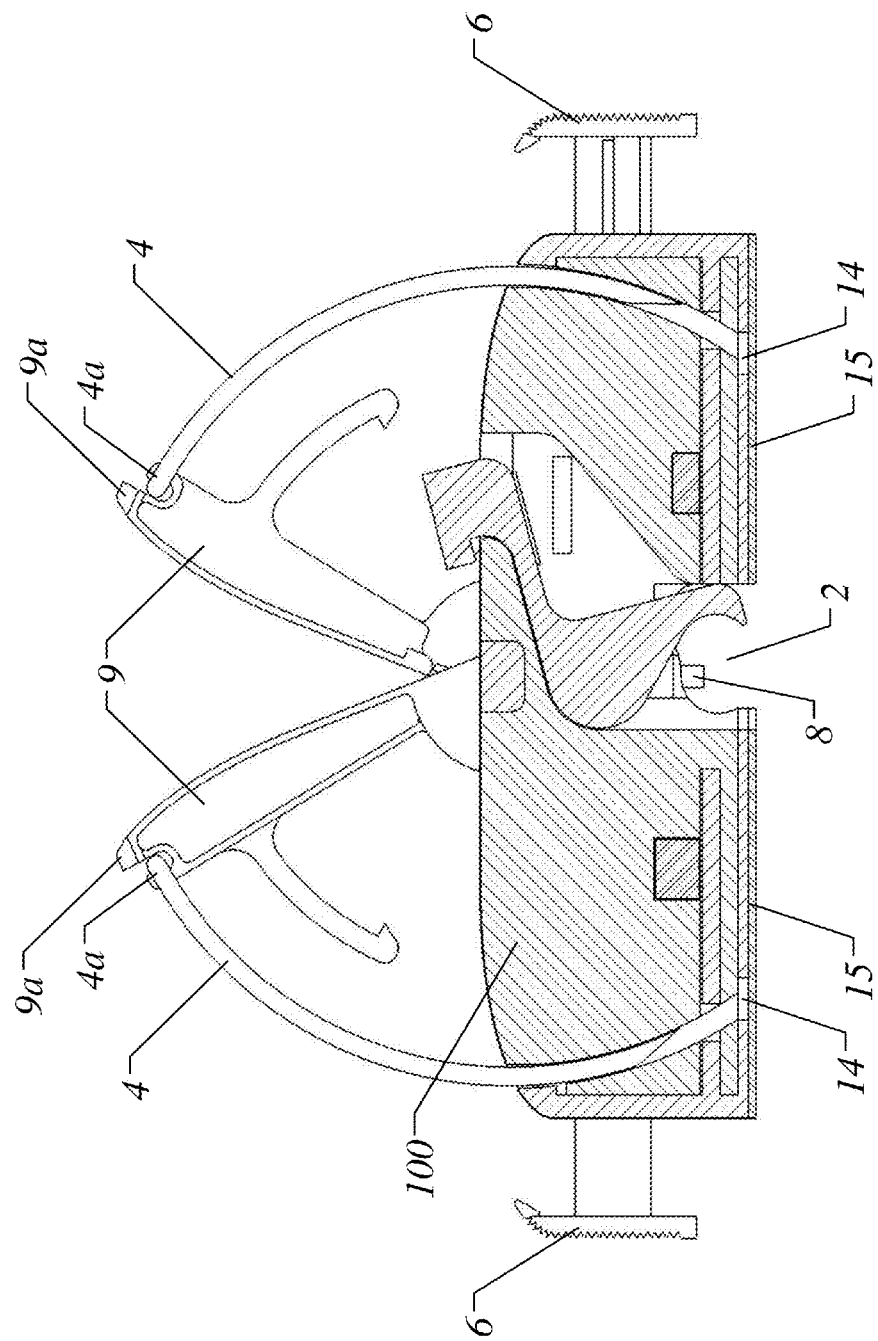
FIG. 2 is a cross-sectional side view of the catheter anchoring device of FIG. 1 in the undeployed position.
Figure 7:
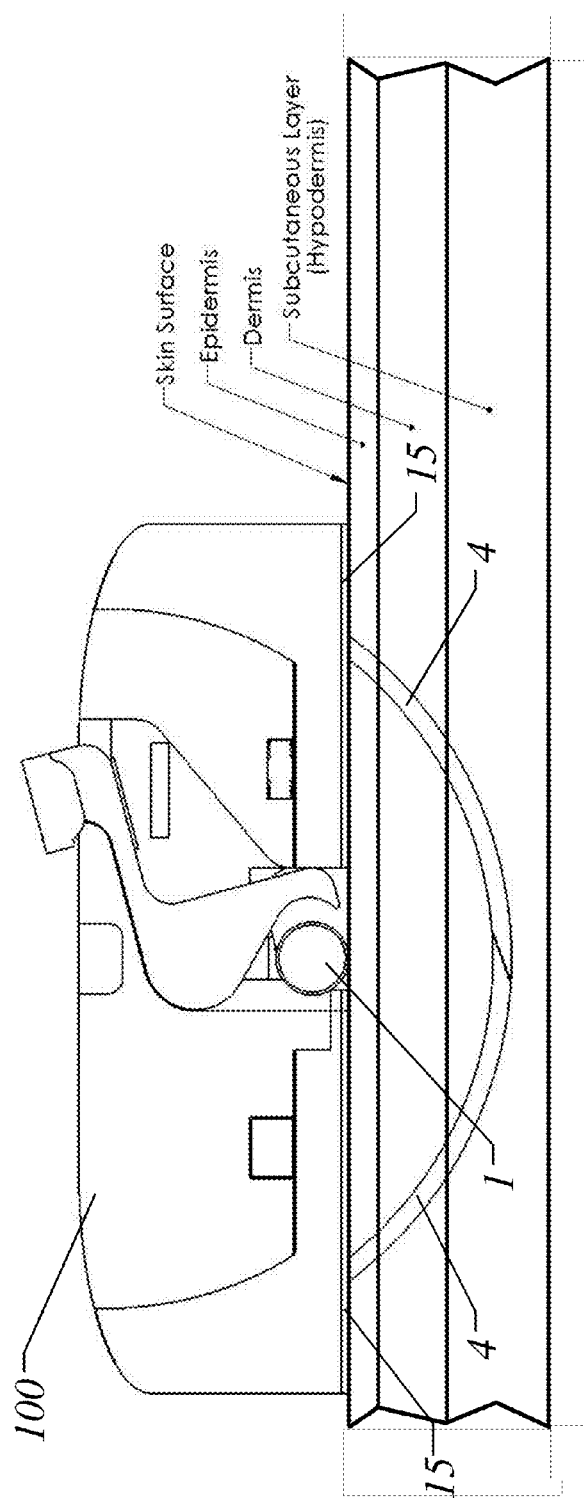
FIG. 7 is a side view of the catheter anchoring device of FIG. 1 in the deployed position with the catheter unlocked and a cross-sectional view of the layers of the patient's skin.

The sharpened tips of both pairs of parallel radial sharps 4 remain locked within housing 100 of the device until the buttons 6 are pressed toward each other as shown in FIG. 2. Both pivoting wings 9 rotate about a common axle 10 in opposite directions. A torsion spring 16 also rotates about axle 10 and is captured between pivoting wings 9. The ends of torsion spring 16 are mechanically coupled to each pivoting wing 9 so that equal and opposite force is applied to each pivoting wing 9 to cause rotation toward its fully open position which is limited by a preset mechanical interference between both pivoting wings 9. In the disengaged position, torsion spring 16 is slightly tensioned. The torsion spring 16 is further tensioned by the rotation of the pivoting wings 9 away from their fully disengaged position. Each pivoting wing 9 contains an integral pinion gear 9b at the opposite end from its respective tang 9a. Each integral pinion gear 9b rotates perpendicular to the rotation of pinion gear 7a and engages the integral teeth of rack 12 on the top surface of the common rack 12. Each rack 12 also has teeth on the perpendicular surface facing the center of the device which engages pinion gear 7a. No motion of the pivoting wings 9 can take place until catheter locking pin 8 has been displaced by a catheter 1 placed within the catheter channel 2 and the catheter anchoring device has been pressed firmly against the surface of the patient's skin by the operator. When the catheter locking pin 8 has been pushed upwards against its integral leaf spring to its unlocked position, the buttons 6 can be pressed inward toward each other. As buttons 6 are pressed toward each other, racks 12 move parallel to the surface of the patient's skin while simultaneously engaging pivoting wings 9 via their respective integral pinion gears 9b. The parallel rack and pinion gear 7 synchronizes the motion of the pivoting wings 9 so that each pivoting wing 9 moves with equal force and distance relative to the surface of the patient's skin. As buttons 6 move closer together, pivoting wings 9 rotate around common axle 10, and pivoting wings 9 are rotated down toward the top surface of the housing of the device. This in turn drives the sharpened ends of each pair of radial sharps 4 through their respective grooves 13 in the housing 100. As the sharpened end of each radial sharp 4 protrudes below the bottom surface of housing 100 though its respective outlet hole 14 as shown in FIG. 2, the sharpened point of each radial sharp 4 pierces membrane 15 that covers the entire bottom surface of housing 100 of the catheter anchoring device. Membrane 15 is made of a soft and pliable material that will not irritate the skin such as silicone. Membrane 15 may be nominally 0.5-1 mm thick. When each radial sharp 4 penetrates the membrane 15, the membrane 15 will seal around the outer diameter of the radial sharp 4. This in turn will keep biological fluids and contaminants (blood, exudates, effluence, etc.) from entering the housing and potentially causing an infection to the patient. As the radial sharps 4 are driven through the bottom surface of membrane 15, the pointed ends of sharps 4 pierce the surface of the patient's skin and penetrate through the epidermis and dermis layers into the subcutaneous layer of the patient's skin as shown in FIG. 7.

Figure 8:
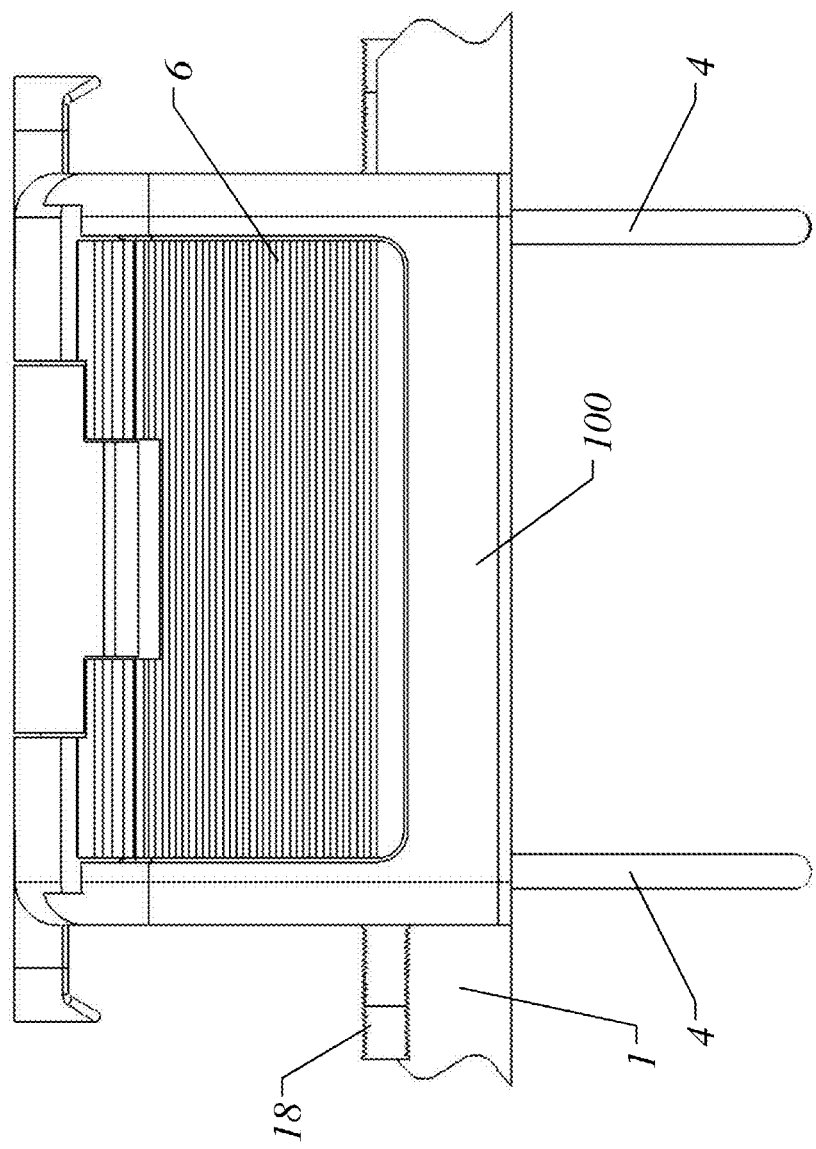
FIG. 8 is an end view of the catheter anchoring device of FIG. 1 in the deployed position.
Figure 9:
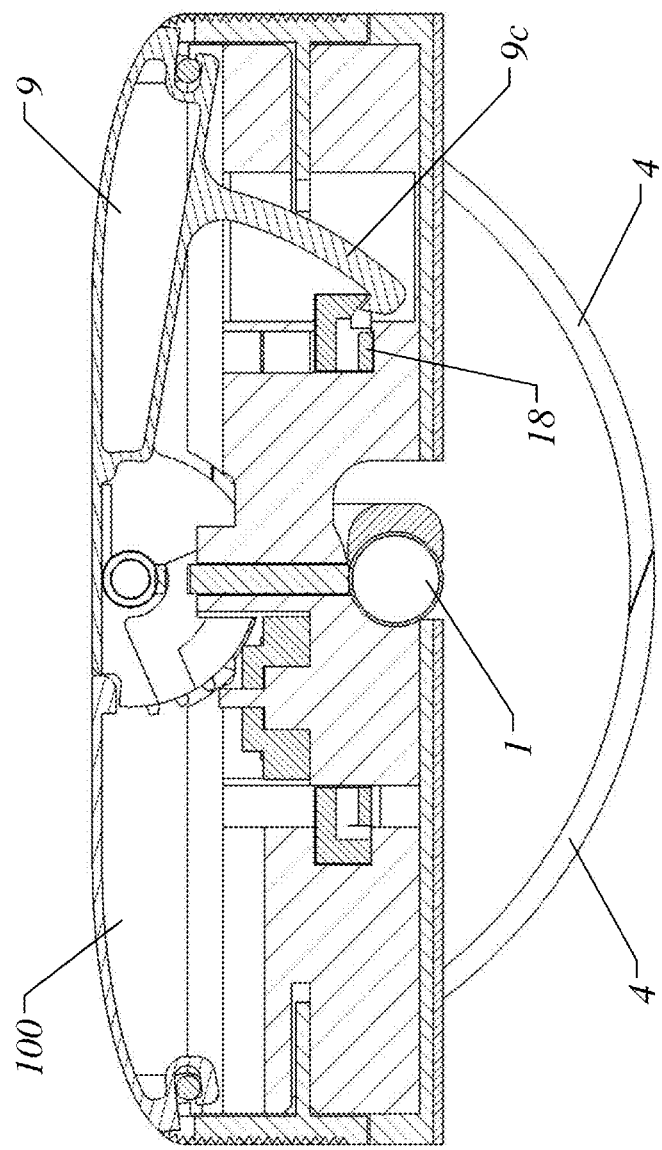
FIG. 9 is a longitudinal cross-sectional side view of the catheter anchoring device of FIG. 1 in the deployed position showing the latching mechanism.

When buttons 6 have been engaged fully and are flush with housing 100 of the device, the two pairs of diametrically opposed radial sharps 4 will be fully deployed underneath the patient's skin at a maximum depth of approximately 4-5 mm in the subcutaneous layer of the patient's skin. The oppositely sharpened tips of each pair of diametrically opposed radial sharps 4, having mating oppositely-formed angular tips, will nest with each other at the nadir below the surface of the patient's skin, consequently forming a virtually solid arc as seen in FIG. 7. The two pairs of parallel diametrically opposed sharps 4 spaced by nearly the full width of housing 100 as shown in FIG. 8 will form a solid and secure anchor to the patient's skin. When buttons 6 have been fully engaged, the integral pawl at the end of each locking arm 9c will latch on the bottom surface of a release bar 18 located in its first detent position in housing 100 as shown in FIG. 9, locking each pivoting wing 9 into the fully deployed position until released by the operator.

The top surfaces of pivoting wings 9 will be flush with the top surface of housing 100 in the fully deployed position.

Figure 10:
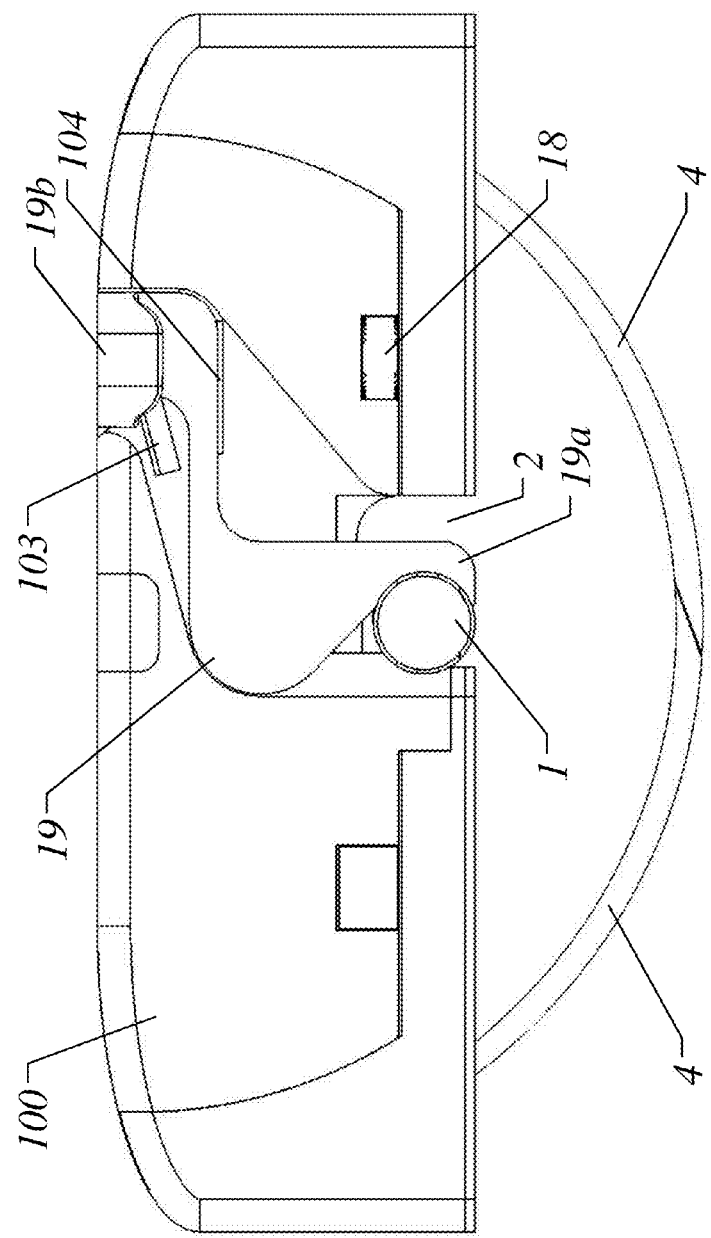
FIG. 10 is a side view of the catheter anchoring device of FIG. 1 in the deployed position with the catheter locking mechanism deployed.

With the catheter anchoring device fully attached to the patient and locked in position, the catheter 1 can be secured to the catheter anchoring device by means of catheter lock 19. In the unlocked position, catheter lock 19 is held in place by a pair of diametrically opposed integral pawls in integrated handles 19b located on either side of catheter lock 19. Each pawl engages a respective detent 103 on each respective side of housing 100. Catheter lock 19 rotates along an axis in housing 100 parallel to the catheter 1 and directly above catheter channel 2. The concave surface of catheter clamp 19a of catheter lock 19 is coated with a thin layer of non-slip pliable material such as silicone. The inner concave face of catheter channel 2 that is opposite the concave surface of catheter clamp 19a may also be coated with a thin layer of non-slip pliable material such as silicone to provide additional frictional resistance to catheter 1 when catheter clamp 19a is in its locked position. When handles 19b on either side of catheter lock 19 are pushed down toward the patient by the operator (e.g. using the operator's thumb and forefinger), each pawl in each respective handle 19b are released from its respective detent 103. As the operator pushes down on handles 19b, the catheter clamp 19a will rotate toward the catheter 1 in catheter channel 2, compressing the side of the catheter 1 very slightly but not inhibiting the flow in catheter 1 and gripping the catheter 1 between the catheter clamp 19a and the opposite concave inner sidewall of catheter channel 2. Catheter lock 19 will lock into the sides of housing 100 via a detent 104 on either side of housing 100 engaged by each respective pawl in handle 19b when the top surface of handles 19b are flush with the top surface of housing 100. In addition to locking the catheter lock 19 in place, the detents 104 and mating channels contained within housing 100 for handles 19b prohibit over-travel of the catheter lock 19 which in turn prohibits the catheter clamp 19a from inhibiting the flow in catheter 1. FIG. 10 shows the side view of the catheter anchoring device with catheter lock 19 locked in place by handles 19b having engaged detents 104 and catheter 1 securely gripped between the concave inner sidewall of catheter channel 2 and the deployed catheter clamp 19a. The resistance provided by the tensioned concave and silicone-coated catheter clamp 19a and the opposite inner concave sidewall of the catheter channel 2 (which may also be coated with silicone) on either side of the catheter 1 within catheter channel 2 along the entire length of catheter channel 2 are sufficient to keep the catheter 1 securely clamped in place (i.e. no movement of the catheter can take place once catheter lock 19 has been rotated into its detent locked position).

Once the catheter 1 has been locked in place, it will remain secured until the catheter 1 and the catheter anchoring device are removed by the operator. The catheter 1 can be axially repositioned, if necessary, without removing the catheter anchoring device from the patient's skin. In the event of such repositioning the operator can unlock catheter lock 19 by pulling the two handles 19b of catheter lock 19 away from the side of housing 100 slightly and orthogonal to the side of housing 100 and in the opposite direction from each other. This action releases the pawls in handles 19b from their respective locked detents 104, and the operator can then rotate the two handles 19b in a direction away from the surface of the patient's skin to release the tension on the catheter clamp 19a and its grip on the catheter 1. This rotational motion will reposition the integral pawls in handles 19b into detents 103 which will keep catheter clamp 19a away from the catheter 1. With the catheter 1 now free to move within the catheter channel 2, the operator can reposition the catheter 1 to its new position, and catheter lock 19 can be re-locked via the methodology described above to re-secure the catheter 1 in its new position. This process may be repeated as many times as needed by the operator.

During the time that the catheter anchoring device is attached to the patient, the surface of the skin surrounding the insertion points of the sharps 4 may be cleaned with an appropriate disinfecting solution such as Betadine. A saturated swab or pad of disinfectant may be wiped and/or squeezed at the surface of the patient's skin adjacent to the sides of the housing 100. The disinfectant will wick under the bottom surface of the catheter anchoring device near the sharp insertion sites, keeping them free of potential infections. This process can be repeated as needed while the catheter anchoring device is attached to the patient's skin.

The catheter anchoring device may be removed easily at any time after it is attached to the patient's skin by the operator. The process for removal has been specifically designed to be easy but deliberate to operate in order to obviate an accidental removal of the catheter anchoring device that could have deleterious repercussions for the patient. A safety mechanism is employed which requires both of release bars 18 to be actuated in order to disengage the locks that hold the catheter anchoring device in place. Therefore, actuating only one release bar will not disengage the locking mechanism that keeps the sharps 4 in their deployed positions which in turn keeps the catheter anchoring device securely attached to the patient's skin.

Figure 11:
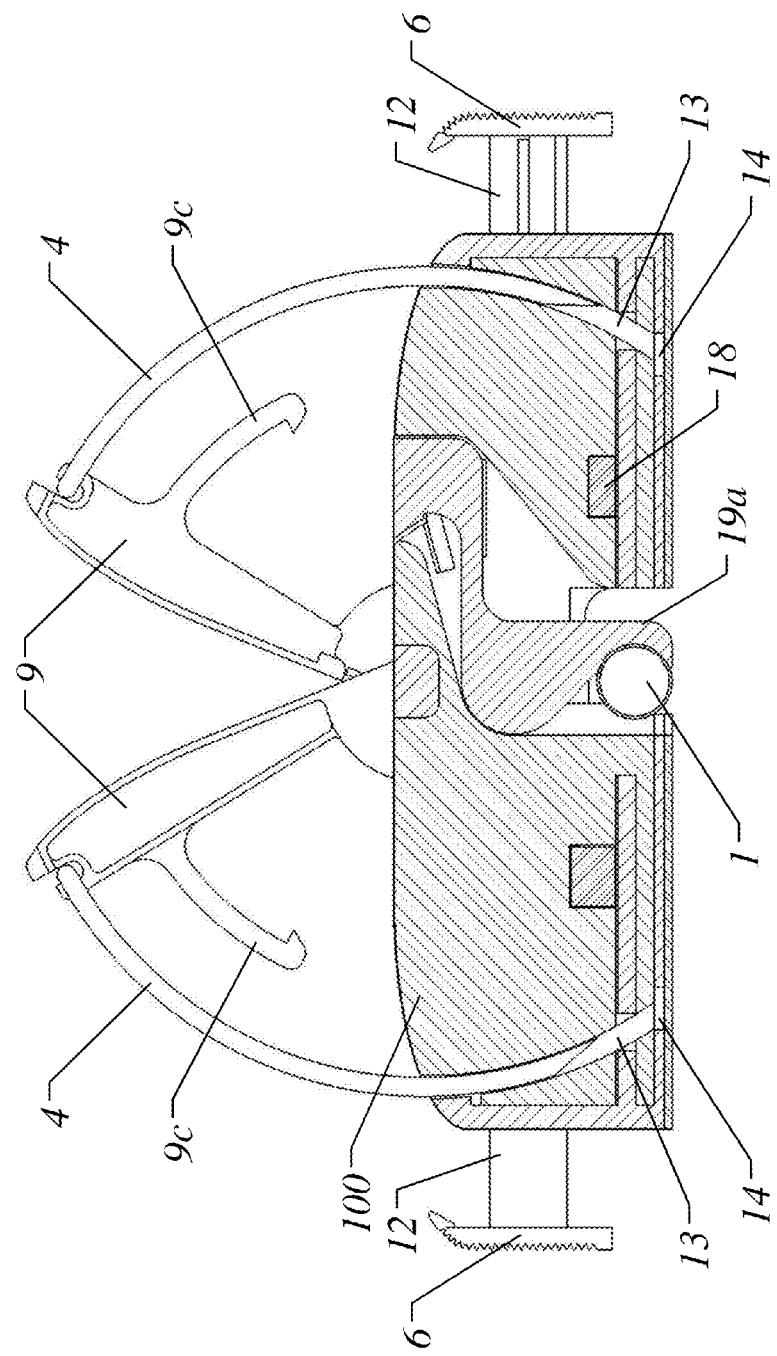
FIG. 11 is a longitudinal cross-sectional side view of the catheter anchoring device of FIG. 1 in the released position.

To remove the catheter anchoring device from the patient's skin, the operator grasps either one of two release bars 18 protruding from the opposite sides of housing 100 (the order of actuation is inconsequential) between his/her thumb and forefinger via its integral ridged grip and pulls release bar 18 to its second detent position. Pulling the release bar 18 to its second detent position accomplishes two mechanical functions simultaneously. First, the pawl at the end of locking arm 9c in the respective pivoting wing 9 will be unlatched from the underside of release bar 18 via a slot in the release bar 18 that is slid into position in the second detent position. Second, release bar 18 is permanently locked into a detent in housing 100 via a pawl on the underside of release bar 18 which is attached to release bar 18 by a flexible member as shown in FIG. 5. Consequently, release bar 18 cannot be re-engaged once the operator has pulled release bar 18 into the second detent position, prohibiting the reuse of the intentionally disposable catheter anchoring device. Once the first release bar 18 has been locked into its second detent position, the operator repeats the procedure with the second release bar 18 on the opposite side of housing 100. Pulling the second release bar 18 into its second detent position accomplishes the same two mechanical functions as the first release bar 18 as described above. Upon unlatching of the pawl at the end of locking arm 9c in the respective second pivoting wing 9, the tensioned torsion spring 16 instantly recoils to its relaxed and undeployed position, pulling both pivoting wings 9 to their original undeployed positions via their integral pinion gears 9b acting on their respective racks 12. As pivoting wings 9 spring back toward their undeployed positions, the two pairs of parallel sharps 4 are retracted from the patient's skin nearly instantly and the sharpened ends of sharps 4 are encapsulated completely within housing 100 within their respective grooves 13 as shown in the cross-sectional view in FIG. 11. Torsion spring 16 has sufficient force to remove all four radial sharps 4 simultaneously from the patient's skin virtually instantaneously. Torsion spring 16 also simultaneously forces racks 12 to their respective undeployed positions where a pawl on a flexible member at the internal end of each respective rack 12 latches onto each respective release bar 18 in its second detent position, permanently locking racks 12, pivoting wings 9, and pinion gear 7a of mechanism 7 in the undeployed position thus preventing any re-engagement of the catheter anchoring device. Consequently, the sharpened ends of radial sharps 4 which are now fully contained and locked within housing 100 cannot be exposed to the operator or anyone else ever again, completely obviating any chance for an inadvertent needlestick injury.

Figure 12:
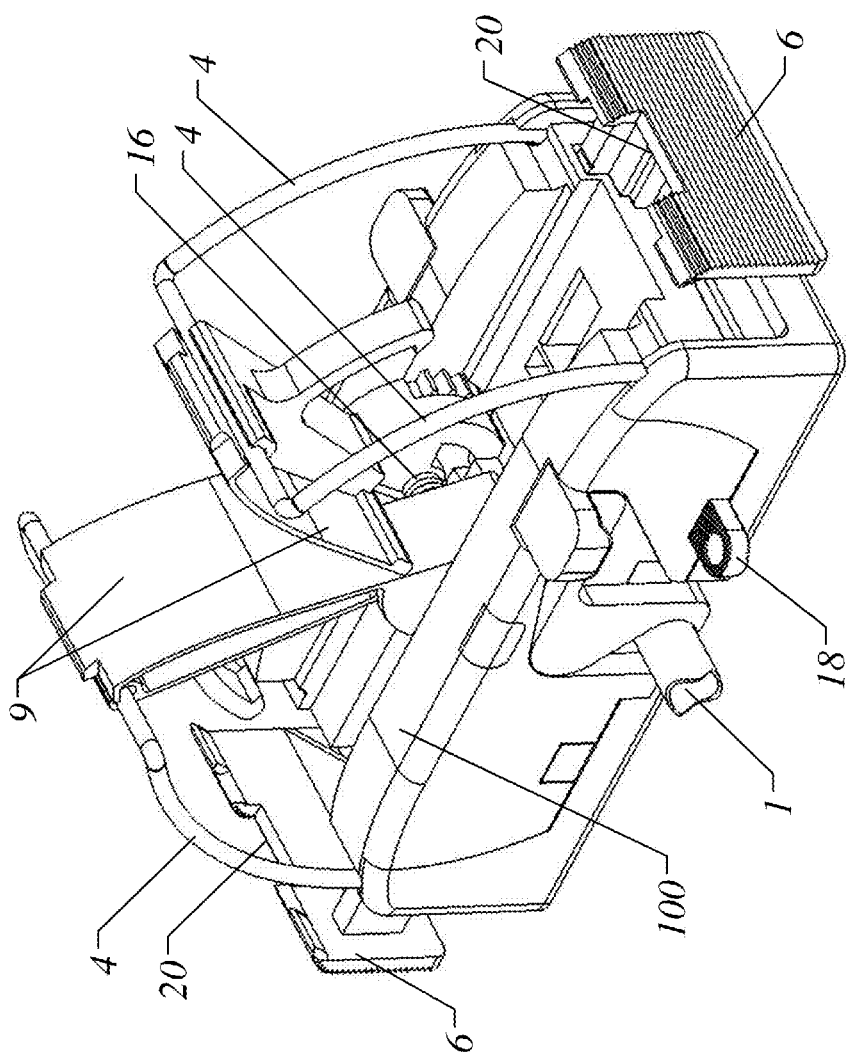
FIG. 12 is a perspective view of the reverse side of the catheter anchoring device of FIG. 1 in the released position.

In the unlikely event that the mechanism to automatically release the spring-loaded sharps 4 from the patient's skin fails to operate as intended, a backup failsafe mechanism can be manually manipulated by the operator to release radial sharps 4 from the patient's skin. A small opening 20 (as shown in FIG. 12) in each button 6 enables the operator to insert a small tool such as a Kelly clamp or the head of a small flat-bladed screwdriver into opening 20 to force the pivoting wing 9 to disengage. This will force the second pivoting wing 9 to disengage, allowing torsion spring 16 to return both pivoting wings 9 to their undeployed positions. In this scenario, the operator should apply a small amount of force to overcome the malfunctioning release bar 18. Even using this manual backup procedure, the operator is fully protected from an inadvertent needlestick injury since the torsion spring 16 will still perform as intended. Additionally, a hole in each release bar 18 is provided as a backup mechanism as a means for pulling the release bar 18 into the second detent position in the event that the operator cannot pull release bar 18 with his or her fingers (e.g. if the release bar 18 becomes slippery due to liquid, blood, or effluence). The operator may also use a Kelly clamp or other small tool to grasp the release bar 18 via the hole in its surface to pull release bar 18 into its second detent position.

The methodology described above for removal enables the operator to dispose of the catheter anchoring device with the catheter 1 still attached. Alternatively, the operator may unlock catheter lock 19 before engaging the release mechanism via release bars 18 as previously described. Using this methodology, the catheter anchoring device and catheter 1 can be removed from the patient and disposed of separately. In either scenario, the protection against an inadvertent needlestick injury to the operator or anyone else is exactly the same.

In the embodiment described above, housing 100 and all of the internal components as seen in FIG. 5 with the exception of the parts noted above that are made of a pliable material and torsion spring 16 may be constructed from any sterilizable, rigid material that is medically safe to be in contact with a patient's skin including but not limited to plastics and/or metals. Torsion spring 16 is intended (but not limited) to be constructed of a suitable metal such as stainless steel or spring steel with the proper spring properties. Radial sharps 4 and integrated crossbar 4a may be formed from a single piece of wire stock suitable for insertion into the skin of a patient such as hardened surgical stainless steel. Radial sharps 4a can also be coated with a layer of nickel or other suitable material which has properties that reduce the risk of infection. It is the intention of this embodiment that radial sharps 4 are rigid and very difficult to bend or deform. Membrane 15 and the concave inner surfaces of catheter clamp 19a and the sidewall of catheter channel 2 may be made of any material suitable for medical use that is pliable and has frictional characteristics similar to silicone and that will also not irritate the skin. In one embodiment of the catheter anchoring device radial sharps 4 and their integrated crossbars 4a are made of hardened and tempered surgical stainless steel coated with a layer of nickel to reduce the risk of infection, and membrane 15 and the concave inner surface of catheter clamp 19a and the concave inner surface of the sidewall of catheter channel 2 are made of silicone. In this one embodiment all other components of the catheter anchoring device except axle 10 and torsion spring 16 as described above are made from a rigid injection molded plastic. In this one embodiment axle 10 is made from surgical stainless steel. One of ordinary skill in the art will recognize that a variety of materials and combinations thereof could be used to achieve the properties of the various components of the catheter anchoring device described.

The embodiment described above contains two pairs of diametrically opposed radial sharps 4 that move coaxially. In another embodiment, there may be one pair of diametrically opposed radial sharps or three or more pairs of radial sharps. The two pair of diametrically opposed radial sharps 4 described above are parallel along the same radius of curvature to each other. In another embodiment, the two pair of diametrically opposed radial sharps 4 may be rotated away from each other by a small angle so that when viewed from either end of the catheter anchoring device they form a slightly obtuse angle relative to the center of housing 100 and do not rotate coaxially. This embodiment can add further stability to the catheter anchoring mechanism especially in applications for large diameter catheters. In another embodiment, either or both of the concave inner surfaces of the catheter clamp 19a and the inner sidewall of catheter channel 2 can be coated with a layer of silicone or other non-slip material. In another alternate embodiment catheter lock 19 can utilize a sliding mechanism to move it from its unlocked position into its locked position rather than the rotating mechanism as described. In another embodiment catheter lock 19 can utilize a spring-loaded push on/push off mechanism. In another embodiment, channels may be incorporated into housing 100 that facilitate the delivery of disinfecting fluids to the sharp insertion sites and/or that facilitate the drainage of fluids and wound exudates from the sharp insertion sites.

Figure 12A:
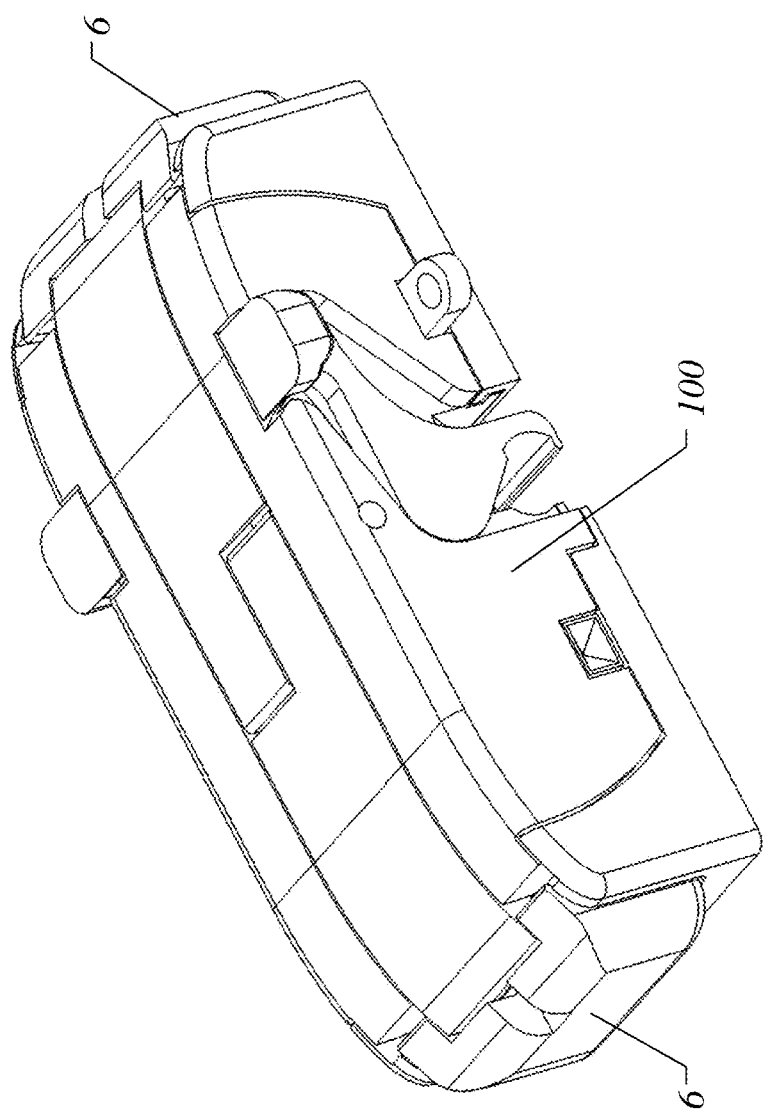
FIG. 12A is a perspective view of the catheter anchoring device of FIG. 1 with the catheter mechanism deployed.

In another embodiment the buttons 6 when fully deployed may extend outward slightly from housing 100 as shown in FIG. 12A rather than rest flush with housing 100. The increased button depth prevents the user's fingers from getting too close to the pivoting wings 9 and minimizing the risk that a user's surgical glove will be inadvertently caught in the pivoting wings 9 as they close and latch during deployment of the catheter anchoring device.

In another embodiment the removal of the catheter anchoring device may be accomplished by pushing both release bars 18 inward toward housing 100 rather than pulling the release bars 18 away from housing 100. This is accomplished by orienting the exposed grips of each release bar 18 through the opposite side of housing 100 from the side of housing 100 as described in the embodiment above. In this embodiment the user pushes the release bars 18 from their first detent positions toward the housing to their second detent positions. The resulting mechanical actuation as described in the embodiment above is then exactly the same upon the second release bar 18 reaching its second detent position provided that the first release bar 18 is also in its second detent position. Similar to the embodiment as described above the order of actuation of each release bar 18 is inconsequential. In another embodiment the release bars 18 may be oriented so that one release bar must be pushed toward housing 100 to move it from its first detent position to its second detent position while the second release bar 18 must be pulled away from housing 100 to move it from its first detent position to its second detent position. In this embodiment as well the order of actuation of each release bar to remove the catheter anchoring device is inconsequential.

In another embodiment each pair of radial sharps 4 are independently connected to each pivoting wing 9 and no crossbar 4a connects the pair of radial sharps 4 to that pivoting wing 9. In this embodiment the mechanical operation of the radial sharps 4 attached to the pivoting wing 9 is the same as described in the first embodiment.

Furthermore, embodiments can to be used to anchor many types and sizes of catheters, drains, electrical catheters such as transvenous pacemaker wires, or nearly any type of other medical conduit that delivers fluids, medicines, or gases to the human body or extracts fluids or gases from the human body—any of such catheters or conduits which may be anchored to a patient's skin while in service. The embodiment described above illustrates a typical example of a catheter anchoring device for a specific catheter size (i.e. the diameter of the catheter). The embodiment described above can be modified to accommodate any specific size of catheter, drain, or medical conduit. For example, for nearly any small diameter catheter, drain, or conduit, the size of the catheter channel 2, inner concave sidewall of the catheter channel 2, and catheter lock mechanism 19 would be scaled appropriately to accommodate the specific catheter diameter. In larger diameter catheter applications such as chest tubes, for example, the entire size of the catheter anchoring device could be scaled and/or the catheter locking mechanism 19 as described above made larger to appropriately accommodate the size of the catheter 1 and provide sufficient anchoring strength to securely hold the catheter 1 in place.

In practice, an operator (typically a physician in the United States) will insert a catheter 1 into a patient using a known methodology. Once the catheter 1 has been inserted, the operator will remove the catheter anchoring device from its factory-sealed package. The catheter anchoring device is fully sterile when it is removed from its sealed packaging. Due to the mechanical interlock failsafe mechanism described above, the four pointed ends of the radial sharps 4 are safely and securely encased within housing 100 of the catheter anchoring device and cannot be deployed accidentally in any way before the device is properly positioned on the patient's skin. The operator cleans the surface of the skin with a disinfecting solution such as Betadine where the catheter anchoring device is to be placed. The operator may also apply a topical anesthetic on the patient's skin. The operator then places the catheter anchoring device on the patient's disinfected skin near the insertion site for the catheter 1. The catheter anchoring device is positioned over the catheter 1 which lies parallel to the surface of the skin so that the catheter 1 lies lengthwise within catheter channel 2. With the outlets for the radial sharps 4 safely pressed against the patient's skin, the mechanical interlock failsafe mechanism is released by the presence of the appropriately-sized catheter 1 within catheter channel 2 which displaces catheter locking pin 8 as the operator presses the catheter anchoring device toward the patient's skin. With one hand the operator grasps the two buttons 6 between his/her thumb and forefinger; and while applying light pressure toward the surface of the patient's skin, the operator squeezes buttons 6 inward deploying radial sharps 4.

The sharpened tips of radial sharps 4 penetrate the membrane 15 on the bottom surface of the catheter anchoring device through outlet holes 14 and enter the surface of the patient's skin. As each radial sharp 4 penetrates membrane 15, the pliable silicone material self-seals around the outer diameter of each radial sharp 4, prohibiting blood, exudates, and other contaminants from being drawn into the separate grooves 13 which guide each individual radial sharp 4. This self-sealing process reduces the risk of infection to the patient while the catheter anchoring device is attached to the patient's skin. As the actuation mechanism is engaged by the operator, the radial sharps 4 penetrate the epidermis, dermis, and subcutaneous layers of the skin. When buttons 6 have been fully engaged by pressing them toward each other and the buttons 6 are flush with housing 100, a positive detent caused by the latching of the pawl on the end of each pivoting wing locking arm 9c onto its respective release bar 18 will be felt by the operator (and an audible click will be heard by the operator as well) to let the operator know that the catheter anchoring device has been locked securely in place. As the catheter anchoring device is locked into its fully deployed position, the oppositely-sharpened ends of each pair of diametrically opposed radial sharps 4 nest into each other forming a nearly solid arc at a preset depth of approximately 4-5 mm beneath the surface of the patient's skin in the subcutaneous layer. This nesting of each pair of the sharpened ends of each pair of radial sharps 4 eliminates the "splinter effect" for the patient. Penetration of the radial sharps 4 to the subcutaneous layer provides maximum holding strength for the catheter anchoring device while reducing potential risks to the patient as previously enumerated and reduces discomfort to the patient while the catheter anchoring device is attached to the patient's skin. When the catheter anchoring device has been secured to the patient's skin, the operator then locks the catheter 1 in place to the catheter anchoring device by pushing down lightly on the handles 19b of catheter lock 19 (e.g. using the operator's thumb and forefinger). When the pawls in each handle 19b engage their respective detents 104 in housing 100, the operator will feel and hear the positive engagement of catheter lock 19 to let him/her know that the catheter 1 is fully locked. The operator may also visually confirm that the catheter 1 is locked in place by catheter lock 19 by noticing that the top surfaces of handles 19b are flush with the top surface of housing 100. As previously described, the engagement of catheter lock 19 very slightly compresses the catheter 1 (without inhibiting its flow) between the concave inner surface of catheter clamp 19a and the inner concave sidewall of catheter channel 2 opposite it. Since one or both concave surfaces are coated in silicone which has non-slip properties, the catheter 1 is held securely once gripped within catheter channel 2 by catheter lock 19.

After confirming the insertion depth of the catheter 1 by x-ray or other means or for any other reason, the operator may reposition the catheter 1 after releasing catheter lock 19 using the procedure described above. Once the catheter 1 has been placed in its new position by the operator, the catheter 1 can be re-secured using the catheter locking procedure described above. This process can be repeated as many times as necessary by the operator without having to detach the catheter anchoring device from the patient's skin. The unlocking mechanism has been designed to be very deliberate in actuation so that the catheter lock 19 cannot be accidentally disengaged by the patient or anyone else, for an accidental dislodgement of the catheter 1 could have serious consequences for the patient. As is standard practice with sutured catheters, the catheter anchoring device can also be covered in medical tape that is attached to the patient's skin after the catheter anchoring device has been secured to the patient's skin if desired. While the catheter anchoring device is attached to the patient's skin, each pair of sharpened ends of the radial sharps 4 are securely nested into each other 4-5 mm below the surface of the patient's skin directly underneath the body of the catheter anchoring device. Consequently, radial sharps 4 which are now contaminated with the patient's blood are prevented from causing an accidental needlestick injury to the operator, any other medical personnel, or anyone else while the catheter anchoring device is attached to the patient's skin. Unlike sutured catheters and other conventional catheter anchoring devices, the ends of the sharps 4 of the embodiments only penetrate the skin once and remain embedded in the skin (i.e. they are not exposed to the air and/or contaminants) until the catheter anchoring device is removed from the patient's skin when sharps 4 are withdrawn from the skin. This further reduces the previously enumerated risks of infection which can be very serious or even fatal for the patient. While the catheter anchoring device is attached to the patient's skin, the four small wound sites as well as the catheter anchoring device itself can be cleaned as often as needed using the procedure described above to reduce the risk of infection.

When the operator wishes to remove the catheter 1 from the patient, the operator may either detach the catheter 1 from the catheter anchoring device via unlocking catheter lock 19 or the operator may leave the catheter anchoring device attached to the catheter 1 for disposal with the catheter 1. Under the first scenario, the operator first disengages catheter lock 19 via the procedure described above. In either scenario, the operator will grasp either of the two release bars 18 with his/her thumb and forefinger using its integral ridged grip and pull it slightly away from housing 100 to its second detent position. The operator will feel release bar 18 lock into its second detent position, and release bar 18 will be locked in place prohibiting over-travel or redeployment of release bar 18. The operator then grasps the sides of the catheter anchoring device with one hand; and with the other hand, the operator grasps the second release bar 18 with his/her thumb and forefinger using its integral ridged grip. When the operator pulls the second release bar 18 away from housing 100 to its second detent position, the failsafe mechanism will unlock. Immediately upon the unlocking of the failsafe mechanism, the tensioned torsion spring 16 will instantly retract all four radial sharps 4 from the patient's skin and safely secure their sharpened ends completely within housing 100. Since the catheter anchoring device prevents removal from the patient's skin before all of the sharpened ends of radial sharps 4 have been safely locked within housing 100, the potential for needlestick injuries to the operator or any other personnel are reduced. Due to the mechanical failsafe interlock that is engaged upon release of radial sharps 4 from the patient's skin, the pointed ends of radial sharps 4 are locked within housing 100 of the catheter anchoring device and are prevented from being accidently redeployed. Therefore, no needlestick injury can occur to the operator, other medical personnel, or anyone else after the catheter anchoring device has been removed from the patient's skin. The catheter anchoring device can then be disposed of safely and properly with or without the catheter attached as described above.

As previously described, the process of attaching the catheter anchoring device can be accomplished in just a few seconds easily by the operator. If less than ideal conditions exist or if a patient is unable to or is unwilling to remain motionless during the insertion procedure, then the extremely quick installation procedure will permit the operator to attach the catheter anchor nearly instantly without risk of a needlestick injury to the operator or injury to the patient. The process of unlocking and relocking the catheter 1 in catheter lock 19 in order to reposition the catheter can also be accomplished in a matter of a few seconds. Lastly, the removal process also takes only a few seconds by the operator to achieve.

In another embodiment, a pair of helical sharps may secure the catheter anchoring device to the patient's skin in place of the two pairs of radial sharps and their associated pivoting wings previously described. Both helical sharps are wound in the same hand, either both wound clockwise or both wound counter-clockwise. Each helical sharp is mounted to and allowed to slide in a vertical groove in a drum with an integral pinion gear that is coaxial with its respective helical sharp, and its axis of rotation is orthogonal to the patient's skin. The helical sharps are guided by helical grooves in the housing. The pitch of each helical sharp is different thus allowing the drums and their sharps to be mounted next to each other. When the pinion gear on the drum is turned by its respective rack, the drum turns the helical sharp in the direction of its winding. This rotates the sharp about its axis; and guided by the grooves in the housing, the sharp is driven downward toward the patient's skin. The pointed end of each helical sharp is sharpened to easily penetrate the patient's skin. At full deployment, the pointed end of each sharp penetrates to the subcutaneous layer of the patient's skin. The windings of the pair of helical sharps are designed so that at full deployment their respective tips come to rest touching each other.

In this embodiment of the catheter anchoring device, a mechanical failsafe mechanism similar to the first embodiment is employed. Due to the fully deployed geometry of the helical sharps, the catheter channel is positioned next to the pair of helical sharps (i.e. off-center) in the housing. In the undeployed position, the sharpened tips of the helical sharps are fully encased within the housing, and the failsafe mechanism prevents the deployment of the sharps until a proper deployment condition has been achieved. A catheter locking pin prevents the movement of the rack and pinion gears until a catheter of proper size is located within the catheter channel and the housing is pressed against a patient's skin. When the catheter locking pin releases the rack, the operator can push the buttons toward the centerline of the device parallel to the surface of the patient's skin which compresses a spring element. The movement of each rack rotates each drum which turns the sharpened end of each helical sharp downward through its respective helical groove in the housing and out through its respective outlet in the housing. The bottom of the housing is completely covered with a layer of silicone similar to the first embodiment. As the buttons are pressed inward, the sharpened ends of the helical sharps pierce the membrane and then penetrate the surface of the patient's skin. When the buttons are fully compressed (i.e. they are flush with the housing), the sharps reach their maximum depth of penetration into the patient's skin and the tips of each sharp come to rest touching point to point in the subcutaneous layer of the patient's skin. A pawl at the end of each rack latches onto its respective release bar in its first detent position to lock the catheter anchoring device securely on the patient's skin in a manner similar to the first embodiment. Similar to the first embodiment previously described, the catheter can be released, repositioned, and re-secured as needed via a catheter locking mechanism as previously described. When the operator wishes to remove the catheter anchoring device, the operator pulls both release bars in a similar manner to the first embodiment to their second detent positions. Upon release of the second release bar by moving it into its second detent position, the pinion gears driving the helical sharps will be freed to rotate. The compressed spring element will instantly relax to its unsprung position which will rotate the drums, retracting the helical sharps from the skin and completely encasing them within the housing. The pawls at the ends of the racks will latch onto the release bars in their locked second detent positions, prohibiting the catheter anchoring device and its helical sharps from being redeployed. The catheter anchoring device can then be safely disposed of by the operator. This embodiment protects the operator, the patient, and any other personnel from an inadvertent needlestick injury in the same manner as the first embodiment.

In another embodiment of the catheter anchoring device, the catheter locking mechanism is an integral part of the failsafe interlock mechanism. In this embodiment, the rotating catheter locking mechanism described in the first embodiment is replaced by a linear push on/push off slide mechanism incorporated into one of the two buttons. A first button operates a pinion gear through two integral parallel racks so that pushing this button inward actuates both pivoting wings and their respective radial sharps simultaneously. Similar to the first embodiment a mechanical failsafe mechanism prevents the deployment of the sharps until the catheter anchoring device has been placed over a catheter of proper size on the patient's skin and pressure has been placed on the device toward the patient's skin. When this condition has been achieved, the catheter locking pin disengages the respective channels in the pivoting wings, releasing the rack and pinion gear mechanism and enabling the operator to deploy the sharps by grasping the device between the operator's thumb and forefinger and pressing the first button inward toward the centerline of the device. The second button on the device remains locked in place until the first button has been fully depressed, the radial sharps have been fully deployed, and the pawls at the ends of the locking arms of the pivoting wings have latched onto their respective release bars.

Once the catheter anchoring device is attached to the patient's skin and in its locked fully-deployed position, the interlock for the second button is disengaged allowing the second button to operate. Pushing the spring-loaded second button to its second detent position slides the concave end of the catheter clamp against the catheter and grips the catheter between the catheter clamp and the concave sidewall of the catheter chamber in a manner similar to the first embodiment. Pushing the button inward slightly releases the button from its second detent position, and the compressed spring returns the button to its first undeployed position. This in turn releases the catheter from the catheter clamp so that it can be repositioned and then subsequently re-secured by the operator. The operator may repeat this procedure as many times as needed.

The operator may remove the catheter anchoring device from the patient's skin in a manner similar to that of the first embodiment described above by pulling both release bars into their second detent positions. Upon release of the second release bar, the radial sharps automatically and nearly instantly fully retract from the patient's skin, and the pointed ends of the radial sharps are locked permanently and safely within the housing of the catheter anchoring device so that no needlestick injury can occur.

Figure 13:
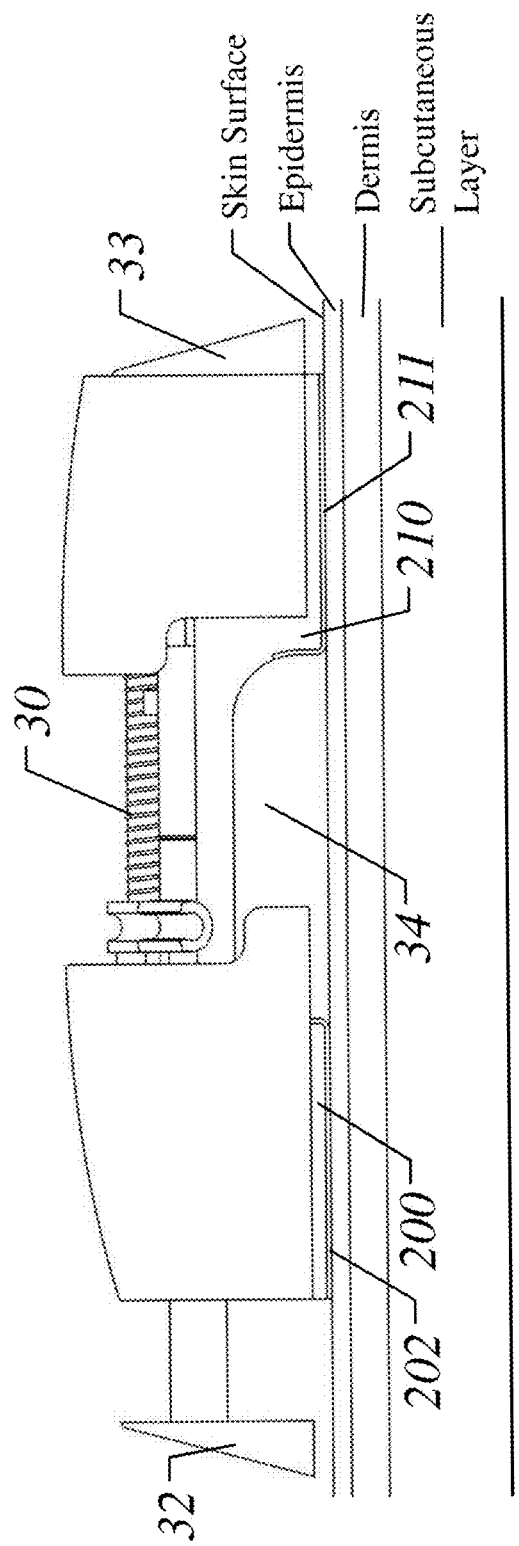
FIG. 13-20 illustrate another embodiment of a catheter anchoring device.

In another embodiment of the catheter anchoring device two pairs of linearly opposed sharps are employed to secure the catheter anchoring device to the patient's skin. In this embodiment, a housing section 200 is connected to a housing section 210 by an integral feature in housing section 210 which mates with a channel 201 (not shown) in housing section 200 in a first detent position shown in FIG. 13. A coiled spring 30 is connected on one end to housing section 200 and on the other end to housing section 210, and in its relaxed position, coil spring 30 keeps housing section 200 and housing section 210 a preset distance apart. Housing section 200 and housing section 210 have flat bottom surfaces that are co-planar, and each bottom surface (202 and 211 respectively) is covered with a layer of non-slip pliable material such as silicone.

Figure 14:
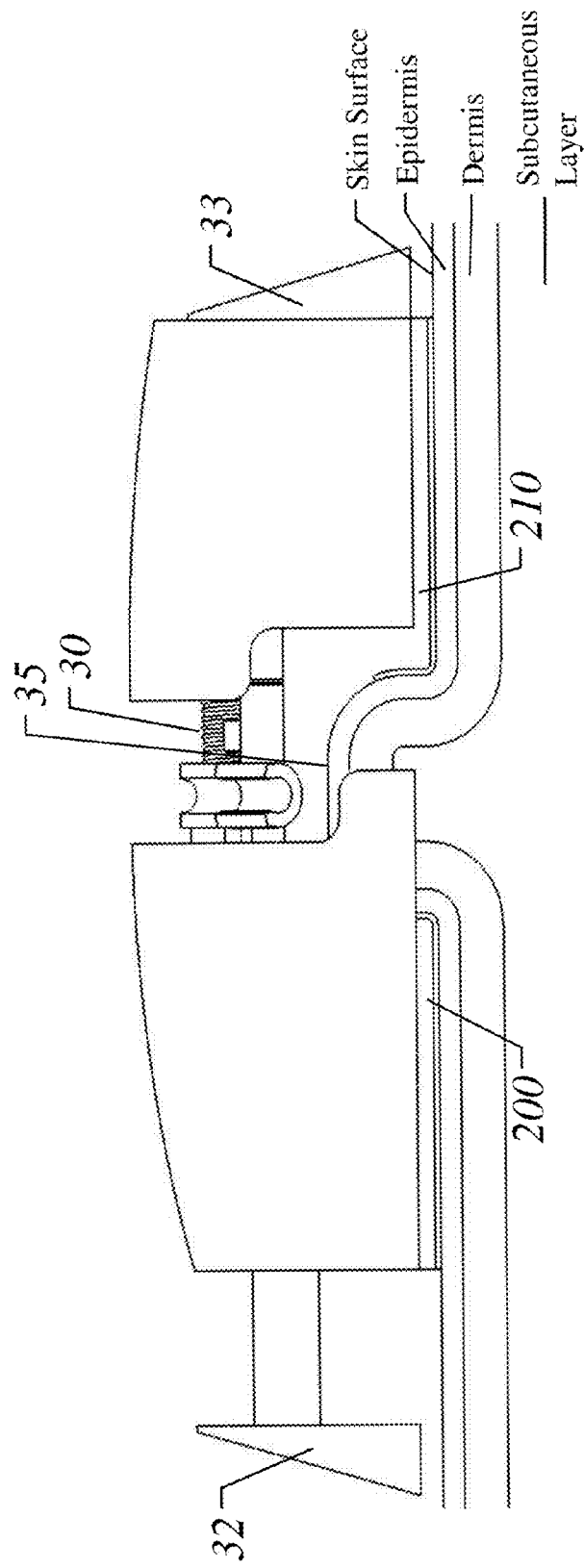

To fasten the catheter anchoring device in this embodiment to the patient's skin, the operator places the flat bottom side of the device on the patient's skin with the longitudinal axis of the device perpendicular to the catheter 100 that has already been inserted into the patient. Using the operator's thumb and forefinger, the operator grips both buttons 32 and 33 on opposite ends of the device. Using light downward pressure to press the silicone covered bottom of the catheter anchoring device onto the patient's skin, the operator squeezes the two housing sections 200 and 210 toward each other. The non-slip surface of the silicone will grip the surface of the skin by friction. As the two sections of the housing are pushed toward each other, the skin is gathered between the two housing sections and will be forced upward and fill skin cavity 34 formed between the housing sections. Skin cavity 34 is designed so that the maximum height of the skin gathered is approximately 5 mm. When housing sections 200 and 210 have reached a preset minimum distance between them as shown in FIG. 14 and the patient's gathered skin has filled skin cavity 34, a skin locking pin 35 (similar to the catheter locking pin in the first embodiment) will be pushed upward against its integral spring by the gathered skin thereby releasing the failsafe interlock mechanism. The release of the failsafe interlock mechanism will then enable a pawl in the integral member of housing 210 to latch onto a detent in housing section 200 which will lock the two housing sections together permanently.

If the operator has failed to gather a sufficient amount of the patient's skin in skin cavity 34, then skin locking pin 35 will prevent the failsafe mechanism from releasing and the two sections of the housing from locking together. In this event the operator may relax the grip on the buttons 32 and 33, and the compressed coiled spring 30 will return the catheter anchoring device to its original undeployed position so that the operator can reattempt to properly deploy the device.

When the skin interlock has been satisfied by the presence of the gathered skin in skin cavity 34 and skin locking pin 35 has been released, buttons 32 and 33 are mechanically freed to move farther inward. Each button acts on a pair of parallel linear sharps 36 that are completely encased within their respective housing section until deployed. The parallel linear sharps 36 can be joined on their non-sharp ends by a crossbar 36a (not shown) that is perpendicular to both sharps. In one embodiment of the catheter anchoring device, each pair of linear sharps 36 and its respective integral crossbar 36a are formed from one continuous piece of surgical stainless steel wire stock. The pointed ends of the sharps 36 are sharpened to easily penetrate the skin, and each pair is sharpened with mating congruent angles for nesting with the opposing pair of sharps 36. Each button acts on each pair of linear sharps 36 through an integral feature that is perpendicular to the surface of the button. Each button also compresses a coiled spring 37 (not shown) as it is pressed toward the center of the catheter anchoring device. When pushed by its respective button, each pair of linear sharps 36 slides toward skin cavity 34 through a channel in its respective housing section. The sidewalls of skin cavity 34 are coated with a thin membrane of silicone so that when the pointed ends of each pair of parallel linear sharps 36 penetrate the sidewall of skin cavity 34 through their respective outlet holes, the membrane will seal around the outer diameter of each linear sharp 36, keeping blood, effluence, and wound exudate from entering the housing.

Figure 15:
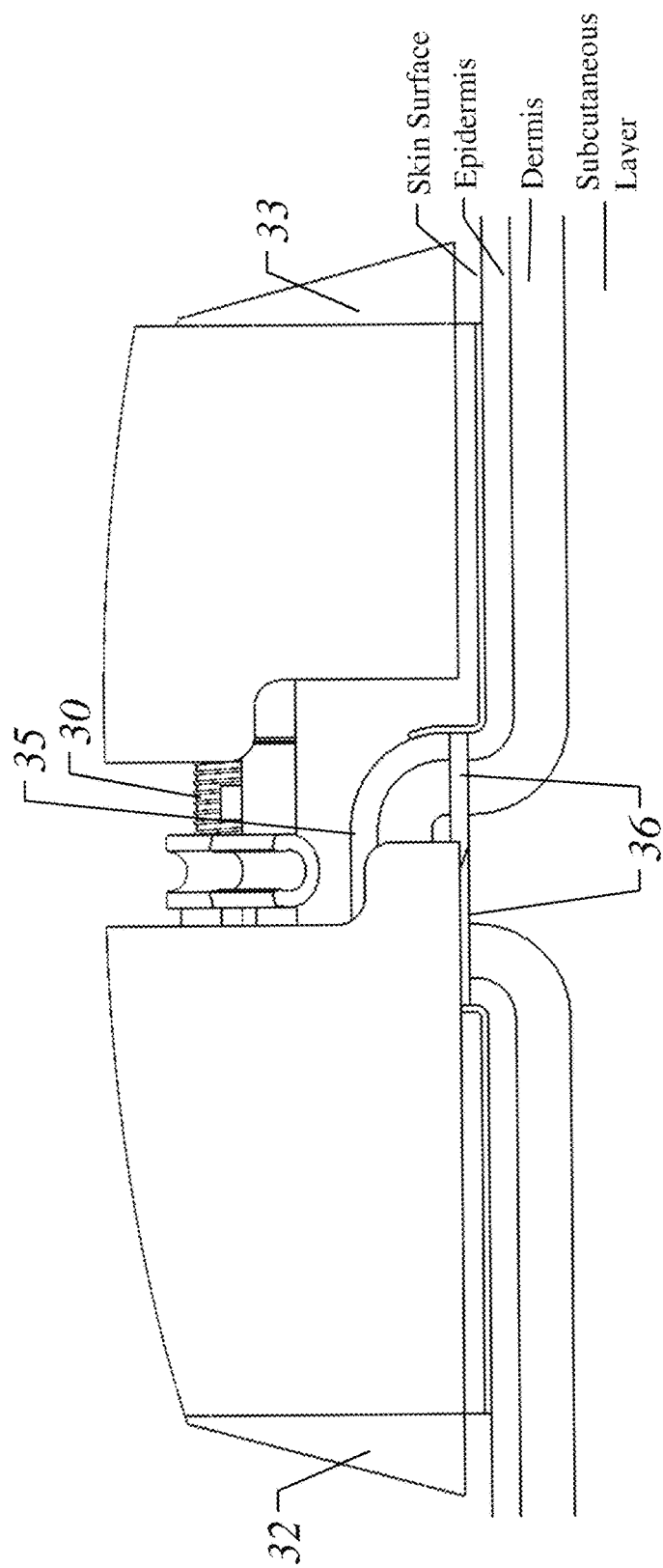
Figure 16:
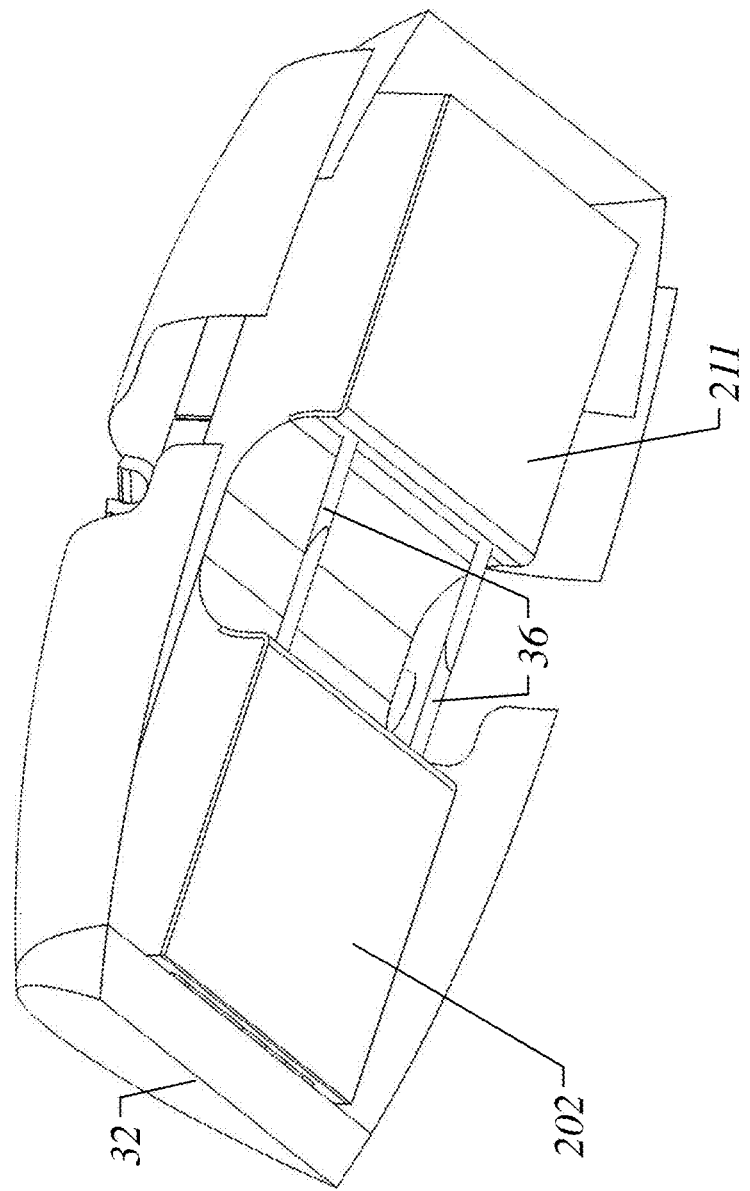

As the operator squeezes buttons 32 and 33 toward each other, the two pairs of linear sharps 36 pierce the membrane of the sidewalls of skin cavity 34 and penetrate the gathered skin of the patient in skin cavity 34. When buttons 32 and 33 are fully depressed and flush with their respective sides of the housing, each pair of sharps 36 will protrude from the sidewall of the housing by half the width of skin cavity 34 parallel to the bottom surface of the housing as shown in FIG. 15. The sharpened points of each opposed pair of sharps 36 will nest with each other due to their mating congruent angles in the subcutaneous layer of the patient's skin gathered in skin cavity 34, forming a nearly continuous linear anchor that will secure the catheter anchoring device to the patient's skin as shown in FIG. 16 and reduce the splinter effect while the catheter anchoring device is attached to the patient's skin. When the buttons are fully deployed, a pawl at the end of each integral feature of buttons 32 and 33 latches onto release bar 38 (not shown) to lock the buttons and the two pairs of parallel linear sharps 36 in place.

Figure 17:
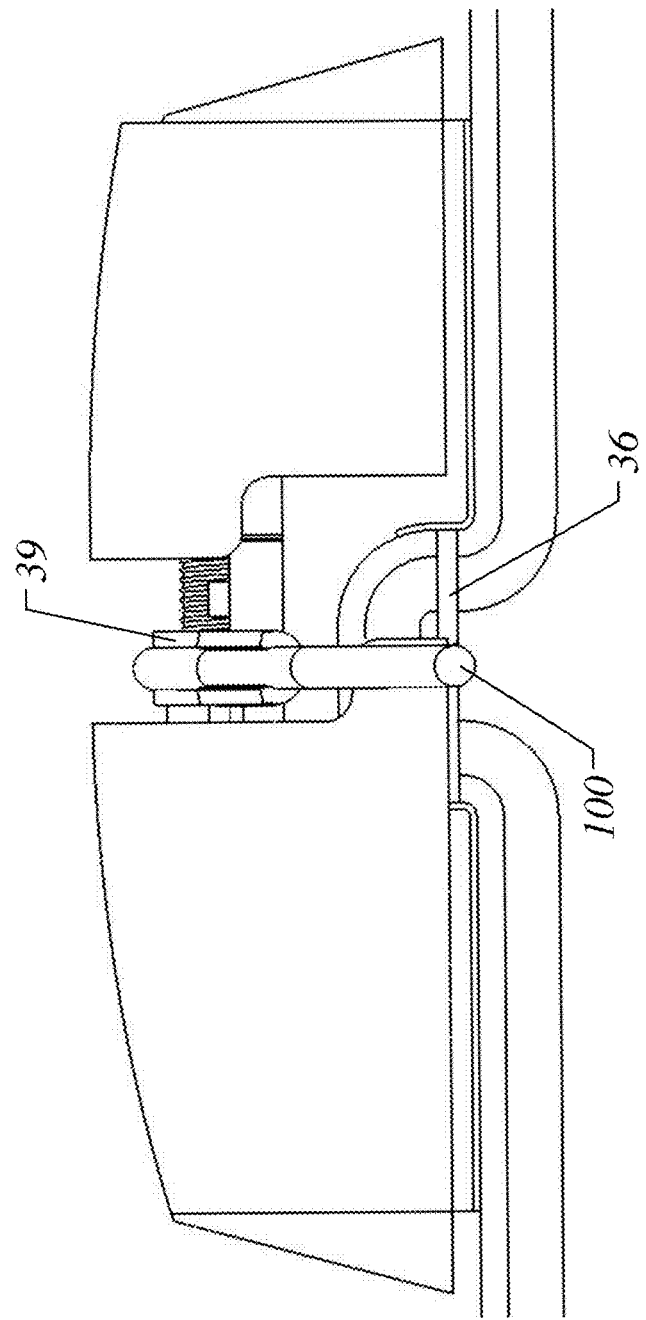

The operator then places catheter 100 in the curved catheter holder 39 as shown in FIG. 17. Catheter holder 39 has tabs emanating from its sides that hold the catheter 100 within its groove. The concave groove surface of catheter holder 39 is coated with a layer of non-slip material such as silicone.

Figure 18:
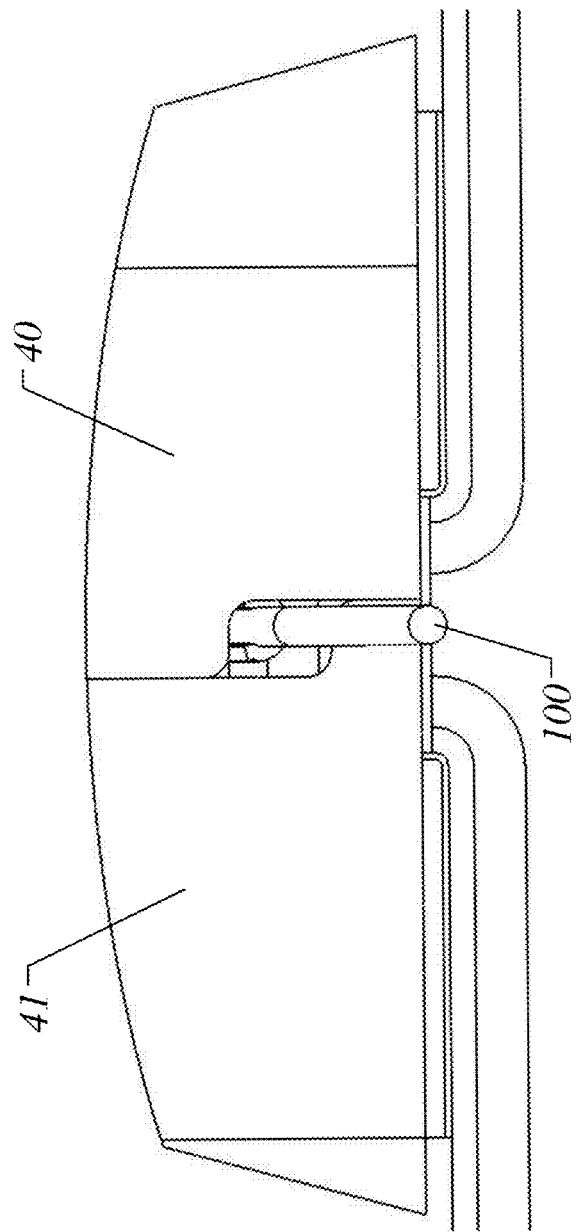

The operator then slides cover 40 toward the center of the catheter anchoring device so that it mates with cover 41 as shown in FIG. 18. Cover 40 has features on the underside of its leading edge which will gently press and hold the catheter 100 into the groove of catheter holder 39 when cover 40 is closed but not impede the flow in the catheter 100. This coupled with the non-slip surface of catheter holder 39 keeps the catheter 100 secured so that it cannot move while cover 40 is closed. A pair of integral pawls in cover 40 lock into a mating pair of detents in housing section 210 to keep cover 40 locked in place.

The operator may reposition the catheter 100 at any time, if necessary, without removing the catheter anchoring device from the patient's skin. The operator can unlock cover 40 when it is in its closed position by using a sliding motion to move cover 40 to its open position, thereby releasing its integrated pawls from their mating detents in housing section 210. The catheter 100 can then be repositioned by the operator since the catheter 100 is free to move within catheter holder 39 while cover 40 is open. The catheter 100 can be re-secured by closing cover 40 and locking it into its closed detent position. This procedure can be repeated as often as necessary.

Figure 19:
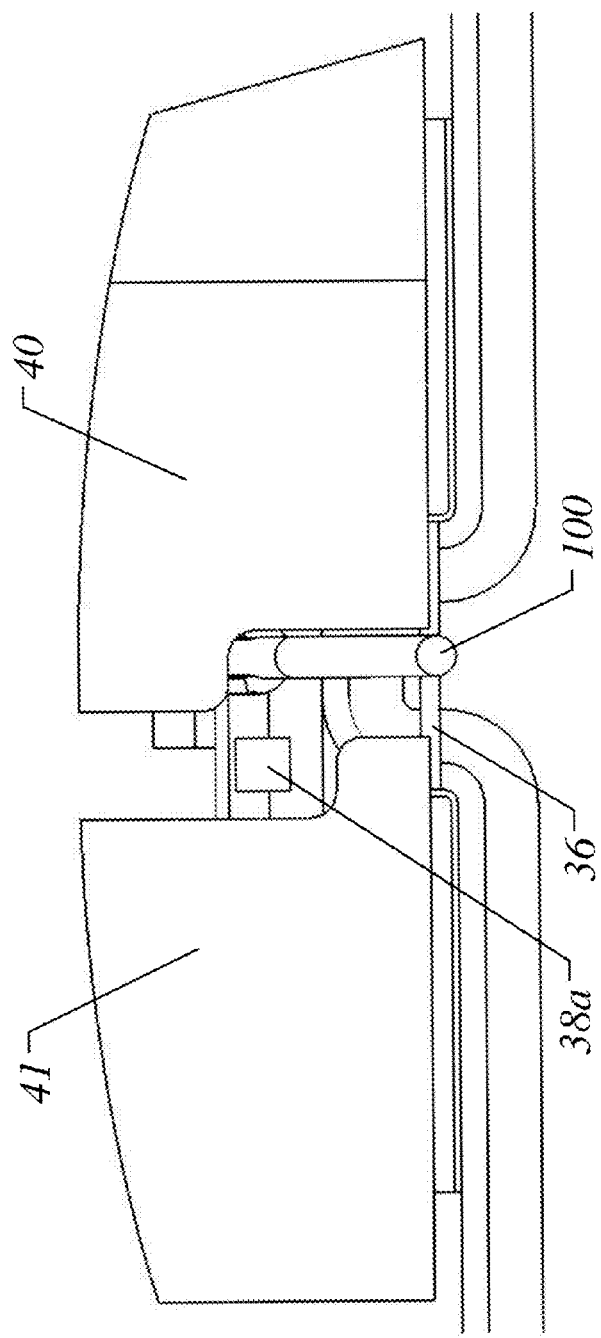
Figure 20:
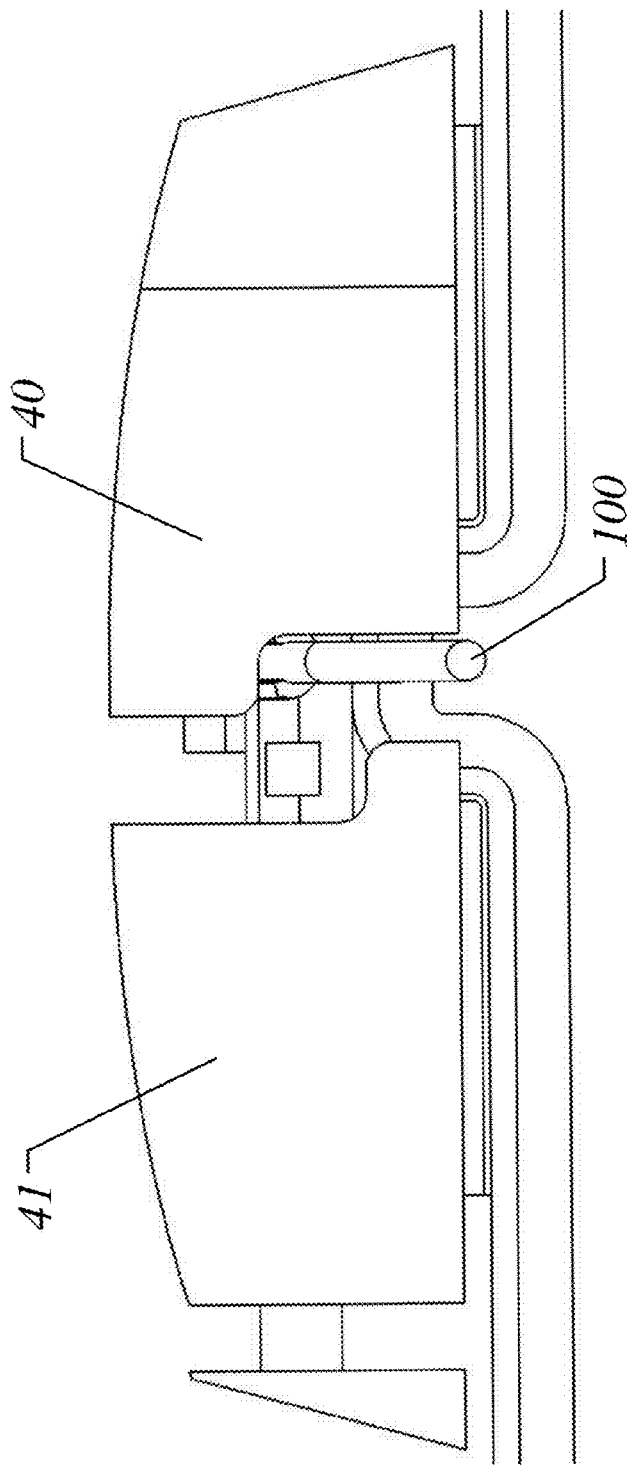

When the operator wishes to remove the catheter anchoring device from the patient's skin, the operator slides cover 41 away from cover 40, overcoming its two integral pawls and their mating pair of detents in housing section 200 that hold cover 41 in its first detent position. This movement as shown in FIG. 19 exposes release button 38a at one end of release bar 38. The operator then pushes release button 38a which moves release bar 38 into its second detent position which accomplishes two mechanical actions simultaneously. First, the pawls at the ends of the integral members of buttons 32 and 33 will be unlatched from release bar 38, and the compressed coil springs 37 acting on each button assembly will return buttons 32 and 33 to their uncompressed state nearly instantly. This will automatically and nearly instantaneously withdraw the opposing sets of parallel linear sharps 36 from the patient's skin and completely encase the two pairs of parallel linear sharps 36 within their respective sides of the housing. Second, release bar 38 will be permanently locked into its second detent position in housing section 200 via a pawl. In order to prohibit the reuse of the catheter anchoring device, pawls on the integral members of buttons 32 and 33 will engage release bar 38, and in turn, this will permanently lock the two pairs of parallel linear sharps 36 safely and completely within their respective sides of the housing. The operator can then safely remove the locked and secured catheter anchoring device from the patient's skin without the risk of a needlestick injury to anyone and safely dispose of the catheter anchoring device. FIG. 20 shows the catheter anchoring device in its fully extracted position with the catheter 100 still secured between catheter holder 39 and cover 40. Alternatively, the catheter 100 can be removed prior to extraction of the catheter anchoring device by sliding cover 40 to its open position and removing the catheter 100 from catheter holder 39.

In the embodiment described above two pairs of parallel linear sharps are specified. Alternatively, this embodiment may contain one set of opposing linear sharps or three or more sets of opposing parallel linear sharps.

In all of the embodiments described, the sharps cannot be deployed before the catheter anchoring device has been placed safely onto the patient's skin and an additional failsafe condition has been satisfied. The catheter anchoring device has to be properly located on the patient's skin and in the case of all but the last embodiment, a catheter of appropriate size has to be within the catheter channel before the catheter locking pin will release the failsafe mechanism. In the last embodiment a similar failsafe mechanism requires that a sufficient amount of the patient's gathered skin must be in the skin cavity before the skin locking pin will release the failsafe mechanism. It is only under this condition that the sharps can be deployed, and consequently, the pointed ends of the sharps can be exposed only to the patient's skin. Therefore, neither the operator nor anyone else can be exposed to the pointed ends of the sharps, obviating any risk of an inadvertent needlestick injury. While the catheter anchoring device is attached to the patient's skin, there is no risk of an inadvertent needlestick injury to the operator or anyone else because the points of the sharps are safely below the housing within the subcutaneous layer of the patient's skin. And since the pointed ends of the sharps are fully retracted from the patient's skin and fully encased and permanently locked within the housing before the catheter anchoring device can be removed from the patient's skin, there is no risk to the operator or anyone else of an inadvertent needlestick injury after the catheter anchoring device has been removed from the patient's skin.

It should be noted that all of the embodiments described use similar techniques as the first embodiment to reduce the risk of infection to the patient. Each of the embodiments may use materials similar to the first embodiment as described. Someone of ordinary skill in the art will recognize that there are many variations and combinations of the embodiments described that can yield the desired attributes of the specific catheter anchoring device embodiments described herein, and the specific embodiments described herein are intended to be illustrative but are not meant to limit the scope of the invention.

It should be noted that conventional catheter anchoring devices for preventing needlestick injuries can easily have their sharps accidentally engaged prior to insertion and/or after their removal processes have been performed because they do not contain failsafe interlock mechanisms to such actions. Consequently, operators who use some conventional catheter anchoring devices could be vulnerable to inadvertent needlestick injuries and their resultant risks. Furthermore, there is nothing to prevent these conventional catheter anchoring devices from being redeployed after removal from a patient's skin which could not only result in an accidental needlestick injury but could also result in contaminating the patient with a serious infection. Unlike conventional catheter anchoring devices, the chance of a needlestick injury during the insertion or removal process or anytime the catheter anchoring device is not attached to the patient (either prior to insertion or after removal) is reduced since the mechanical interlock mechanism locks the pointed ends of the sharps safely and completely within the housing and prohibits the pointed ends of the sharps from being exposed in any way to anyone. The failsafe mechanical interlock only enables deployment of the sharps if the catheter anchoring device is on the surface of a patient's skin (where the ends of the sharps can only be exposed to the patient) and a catheter of proper diameter is present in the catheter channel as would be the case in a proper application of the catheter anchoring device. Furthermore, the only time that the pointed ends of the sharps can be exposed is when they are beneath the surface of the patient's skin, and consequently, they do not pose a risk of a needlestick injury to the operator or anyone else. The pointed ends of the sharps are retracted (which occurs instantly by spring action) in order to remove the catheter anchoring device from the patient's skin, thus reducing the risk of a needlestick injury to the operator or anyone else.

It should be noted that while the foregoing has been described for use with human patients, embodiments of the catheter anchoring device may be used for veterinary patients in a similar fashion.

The preceding description of the invention has been described with reference to various specific embodiments for the purposes of illustration and description, but it is not intended to be exhaustive or to limit the invention to the precise form disclosed. Numerous modifications and variations are possible within the scope and spirit of the inventive concepts described.

Having thus described at least one illustrative embodiment of the invention, various alterations, modifications, and improvements will readily occur to those skilled in the art. Such alterations, modifications, and improvements are intended to be within the spirit and scope of the invention. Accordingly, the foregoing description is by way of example only and is not intended as limiting. The invention is limited only as defined in the following claims and the equivalents thereto.

What is claimed is:

1. An anchor device, the device comprising:
   a housing having a bottom surface;
   at least one pair of sharps, each sharp in the at least one pair of sharps having an end configured to pierce a skin surface;
   a locking mechanism configured to maintain the end of each sharp within the housing when the locking mechanism is engaged and to enable the end of each sharp to protrude from the bottom surface and to pierce a skin surface when the locking mechanism is disengaged;
   a first release bar and a second release bar configured to move from a first detent position to a second detent position, wherein the end of each sharp is configured to protrude from the bottom surface when the first release bar and the second release bar are in the first detent position and remain enclosed within the housing when the first release bar and the second release bar are in the second detent position; and
   at least one spring configured to apply a force to the at least one pair of sharps when the end of each sharp protrudes from the bottom surface and retract the end of each sharp within the housing in response to moving the first release bar and the second release bar from the first detent position to the second detent position.

2. The device of claim 1, wherein the locking mechanism is disengaged by contacting the bottom surface to the skin surface.

3. The device of claim 1, wherein the locking mechanism is disengaged by a catheter.

4. The device of claim 1, the device further comprising:
   at least one button configured to be pressed by an operator to move the at least one pair of sharps when the locking mechanism is disengaged.

5. The device of claim 4, wherein the at least one button moves parallel to the bottom surface of the housing.

6. The device of claim 1, wherein the ends of each pair of sharps are configured to contact each other underneath the skin surface.

7. The device of claim 6, wherein the ends of each pair of sharps are configured to be nested.

8. The device of claim 6, wherein the ends of each pair of sharps touch at a depth from the skin surface.

9. The device of claim 8, wherein the depth corresponds to a dermis layer.

10. The device of claim 8, wherein the depth corresponds to a subcutaneous layer.

11. The device of claim 8, wherein the depth corresponds to the range of approximately 4 millimeters to approximately 5 millimeters.

12. The device of claim 1, the device further comprising:
    a cavity configured to position a catheter; and
    a catheter locking mechanism configured to secure the catheter within the cavity when the catheter locking mechanism is engaged and to allow the catheter to be repositioned when the catheter locking mechanism is disengaged.

13. The device of claim 12, wherein the catheter locking mechanism is engaged after the end of each sharp pierces the skin surface.

14. The device of claim 12, wherein the catheter locking mechanism includes a catheter clamp configured to secure the catheter between an inner surface of the cavity and the catheter clamp.

15. The device of claim 12, wherein the cavity is scaled to fit a dimension of the catheter.

16. The device of claim 1, wherein:
    the at least one spring is further configured to retract the end of each sharp into the housing in response to moving the first release bar and the second release bar from the first detent position to the second detent position.

17. The device of claim 16, wherein the end of each sharp is permanently contained within the housing when the first release bar and the second release bar are in the second detent position.

18. The device of claim 16, wherein the at least one pair of sharps retract simultaneously into the housing in response to moving the first release bar and the second release bar from the first detent position to the second detent position.

19. The device of claim 1, wherein the first release bar and the second release bar permanently reside in the second detent position after being positioned from the first detent position to the second detent position.

20. The device of claim 1, wherein the at least one pair of sharps have a radial configuration.

21. The device of claim 1, wherein the at least one pair of sharps have a linear configuration.

22. The device of claim 1, wherein the at least one pair of sharps have a helical configuration.

23. The device of claim 1, wherein the bottom surface includes a membrane and the end of each sharp is configured to pierce the membrane.

24. The device of claim 23, wherein the membrane is silicone.

25. The device of claim 1, wherein the at least one pair of sharps is stainless steel.

26. The device of claim 1, wherein the at least one pair of sharps is coated with a layer of nickel.

27. An anchor device, the device comprising:
a housing having a bottom surface;
a cavity in the bottom surface;
a locking pin configured to displace away from the bottom surface further into the housing in response to an object being disposed in the cavity when the bottom surface contacts a skin surface;
at least one pair of sharps, each sharp in the at least one pair of sharps having an end configured to pierce the skin surface;
a first spring mechanically coupled to the locking pin and configured to compress in response to displacement of the locking pin away from the bottom surface, allowing movement of the at least one pair of sharps, wherein the first spring is configured to prohibit movement of the at least one pair of sharps when the cavity is empty by mechanically interfering with movement of the at least one pair of sharps;
a first release bar and a second release bar configured to move from a first detent position to a second detent position, wherein the end of each sharp is configured to protrude from the bottom surface when the first release bar and the second release bar are in the first detent position and remain enclosed within the housing when the first release bar and the second release bar are in the second detent position; and
at least one second spring configured to apply a force to the at least one pair of sharps when the end of each sharp protrudes from the bottom surface and retract the end of each sharp within the housing in response to moving the first release bar and the second release bar from the first detent position to the second detent position.

28. The anchor device of claim 27, wherein the cavity is configured to position a catheter, and the anchor device further comprises:
a catheter locking mechanism configured to secure the catheter within the cavity when the catheter locking mechanism is engaged and to allow the catheter to be repositioned when the catheter locking mechanism is disengaged.

* * * * *